United States Patent [19]

Asato

[11] 4,156,670

[45] May 29, 1979

[54] SUBSTITUTED TETRAHYDROBENZOTHIOPHENES AND METHOD OF PREPARATION THEREOF

[75] Inventor: Goro Asato, Titusville, N.J.

[73] Assignee: American Cyanamid Company, Stamford, Conn.

[21] Appl. No.: 912,813

[22] Filed: Jun. 5, 1978

Related U.S. Application Data

[63] Continuation of Ser. No. 669,431, Mar. 23, 1976, abandoned, which is a continuation-in-part of Ser. No. 532,449, Dec. 13, 1974, abandoned, which is a continuation-in-part of Ser. No. 436,827, Jan. 25, 1974, abandoned.

[51] Int. Cl.$^2$ .................... C07D 333/16; A01N 9/00
[52] U.S. Cl. .................... 260/332.3 P; 260/329 F; 260/329 S; 260/329 AM; 260/329 HS; 260/332.2 A; 260/332.3 C; 260/332.5; 424/275; 426/648
[58] Field of Search ..... 260/329 S, 329 HS, 329 AM, 260/329 F, 332.2 A, 332.3 C, 332.3 P, 332.5

[56] References Cited

U.S. PATENT DOCUMENTS 3,998,959   12/1976   Asato et al. .................... 260/332.2 R

*Primary Examiner*—A. Siegel
*Attorney, Agent, or Firm*—Harry H. Kline

[57] ABSTRACT

This disclosure describes novel 4,5,6,7-tetrahydrobenzo[b]thien-4-ylureas useful as herbicidal agents and animal growth regulants and processes for the preparation thereof.

69 Claims, No Drawings

SUBSTITUTED TETRAHYDROBENZOTHIOPHENES AND METHOD OF PREPARATION THEREOF

CROSS REFERENCE TO RELATED APPLICATIONS

This application is a continuation of my copending application, Ser. No. 669,431, filed Mar. 23, 1976 now abandoned, which is a continuation-in-part of my abandoned application Ser. No. 532,449, filed Dec. 13, 1974, which in turn is a continuation-in-part of my abandoned application, Ser. No. 436,827, filed Jan. 25, 1974.

BRIEF SUMMARY OF THE INVENTION

This invention relates to novel 4,5,6,7-tetrahydrobenzo[b]thien-4-ylureas which may be represented by the following general formula:

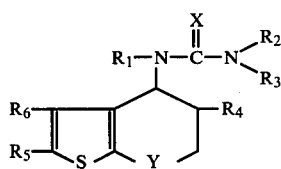

(I)

wherein X is a divalent oxygen or divalent sulfur; Y is a divalent moiety of the formulae:

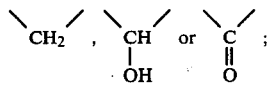

$R_1$ is hydrogen or alkyl $C_1$–$C_4$; $R_3$ is hydrogen, alkyl $C_1$–$C_4$, cycloalkyl $C_3$–$C_6$, allyl, 2-propynyl, benzyl or β-phenylethyl; $R_4$ is hydrogen or alkyl $C_1$–$C_4$; $R_5$ is hydrogen, chloro, bromo or iodo; $R_6$ is hydrogen or alkyl $C_1$–$C_4$; $R_2$ is selected from the group consisting of the substituents listed in Table I below:

TABLE I

| $R_2$ |
|---|
| hydrogen |
| alkyl $C_1$–$C_{12}$ |
| cycloalkyl $C_3$–$C_6$ |
| allyl |
| methallyl |
| 2-butenyl |
| 2-propynyl |
| hydroxy |
| alkoxy $C_1$–$C_6$ |
| allyloxy |
| methallyloxy |
| 2-butenyloxy |
| methoxymethyl |
| —O—CH$_2$—COOH |
| phenoxy |
| benzyloxy |
| —CH$_2$—CH$_2$—OH |
| —CH$_2$—CH$_2$—O—CH$_3$ |
| —CH$_2$—CH$_2$—S—CH$_3$ |
| —CH$_2$—CH(OR)$_2$ |
| —CH$_2$—CF$_3$ |
| —CH$_2$—CN |
| —CH$_2$—CO$_2$R |
| —NH—CO$_2$R |
| —C(=O)—R |
| —C(=O)—CCl$_3$ |

TABLE I-continued

| $R_2$ |
|---|
| (tetralinyl-methyl) |
| (tetrahydrofuranyl-methyl) |
| (tetrahydrofuranyl-C(=O)—NH—) |
| (tetrahydrothiophenyl-methyl) |
| (tetrahydrobenzothienyl-methyl) |
| (tetrahydrobenzothienyl-NH—C(=O)—NH—CH$_2$—) |
| (pyridyl-CH$_2$—) |
| (pyridyl-CH$_2$—CH$_2$—) |
| (Q-phenyl-(CH$_2$)$_n$—) | wherein (in Table I) R is alkyl $C_1$–$C_4$, n is 0, 1 or 2, and Q is selected from the group consisting of the substituents listed in Table II below:

TABLE II

| Q | | |
|---|---|---|
| n = 0 | n = 1 | n = 2 |
| 2-methyl-4-bromo | hydrogen | hydrogen |
| 3,4-methylenedioxy | 4-chloro | |
| 3- or 4-methoxy | 4-methoxy | |
| 4-ethoxy | 3,4-methylenedioxy | |
| 4-chloro | | |
| 4-butoxy | | |
| 4-methylthio | | |
| 2,4-dimethyl | | |
| 2,5-dimethoxy | | |
| 2,4-dichloro | | |
| 4-nitro | | | and $R_2$ and $R_3$ taken together with the associated N(itrogen) is selected from the group consisting of morpholino, piperidino, pyrrolidino, 4-phenylpiperazino, 4-(4-methoxyphenyl)piperazino, 4-carbethoxypiperazino, 4-oxopiperazino, 1,2,3,4-tetrahydroquinolino and the moiety of the formula:

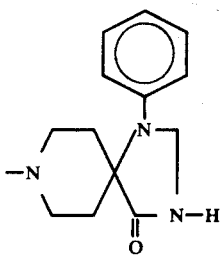

DETAILED DESCRIPTION OF THE INVENTION

A preferred embodiment within the scope of the present invention may be represented by the following formula:

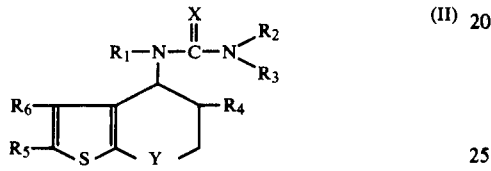
(II)

wherein X, Y, $R_1$, $R_3$, $R_4$, $R_5$ and $R_6$ are as hereinabove defined and $R_2$ is selected from the group consisting of the substituents listed in Table III below:

TABLE III

| $R_2$ |
|---|
| hydrogen |
| alkyl $C_1$–$C_8$ |
| cycloalkyl $C_3$–$C_6$ |
| allyl |
| methallyl |
| 2-butenyl |
| 2-propynyl |
| hydroxy |
| alkoxy $C_1$–$C_6$ |
| allyloxy |
| methallyloxy |
| 2-butenyloxy |
| methoxymethyl |
| phenoxy |
| —$CH_2$—$CH_2$—OH |
| —O—$CH_2$—COOH |
| —$CH_2$—$CH(OR)_2$ |
| —$CH_2$—$CF_3$ |
| —$CH_2$—CN |
| —NH—$CO_2$R |
| $-\overset{\overset{O}{\|}}{C}-R$ |
| $-\overset{\overset{O}{\|}}{C}-CCl_3$ |
| 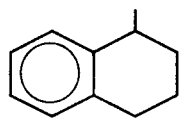 |
| 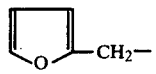 |
| 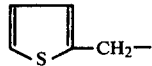 |
| 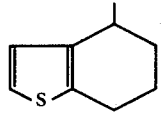 |

TABLE III-continued

| $R_2$ |
|---|
| 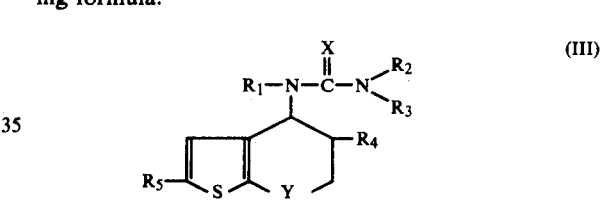 |
| benzyloxy | wherein (in Table III) R and n are as hereinabove defined and Q is selected from the group consisting of the substituents listed in Table IV below:

TABLE IV

| Q | | |
|---|---|---|
| n = 0 | n = 1 | n = 2 |
| 4-chloro | hydrogen | hydrogen |
| 3,4-methylene-dioxy | 4-methoxy | |
| 3- or 4-methoxy | | |
| 4-ethoxy | | |
| 4-butoxy | | |
| 4-methylthio | | |
| 2,4-dimethyl | | |
| 2,4-dichloro | | |
| 4-nitro | | |
| 2-methyl-4-bromo | | |

Another preferred embodiment within the scope of the present invention may be represented by the following formula:

(III)

wherein X, Y, $R_1$, $R_3$, $R_4$ and $R_5$ are as hereinabove defined and $R_2$ is selected from the group consisting of the substituents listed in Table V below:

TABLE V

| $R_2$ |
|---|
| hydrogen |
| alkyl $C_1$–$C_8$ |
| cycloalkyl $C_3$–$C_4$ |
| allyl |
| 2-propynyl |
| hydroxy |
| alkoxy $C_1$–$C_6$ |
| methoxymethyl |
| phenoxy |
| 4-methoxyphenyl |
| 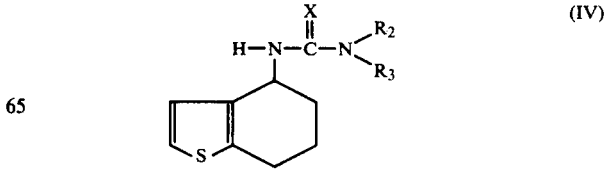 |

Another preferred embodiment within the scope of the present invention may be represented by the following formula:

(IV)

wherein X is as hereinabove defined and R₂ and R₃ taken together with the associated N(itrogen) is selected from the group consisting of morpholino, pyrrolidino, 4-phenylpiperazino, 4-(4-methoxyphenyl)piperazino, 1,2,3,4-tetrahydroquinolino and the moiety of the formula:

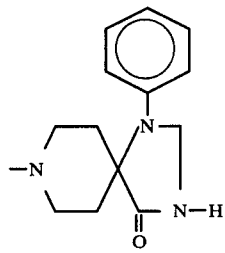

A most preferred embodiment within the scope of the present invention may be represented by the following formula:

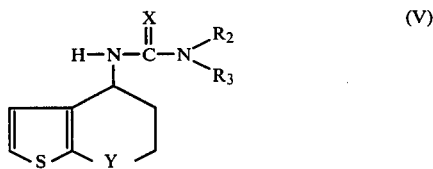

wherein X and Y are as hereinabove defined, $R_2$ is hydrogen, alkyl $C_1$-$C_8$, allyl, alkoxy $C_1$-$C_4$, 2-propynyl, methoxymethyl or hydroxy and $R_3$ is hydrogen or alkyl $C_1$-$C_4$.

Some of the novel compounds of the present invention (VI) may be readily prepared by reacting an appropriately substituted 4,5,6,7-tetrahydrobenzo[b]thiophen-4-amine (VII) with an appropriately substituted isocyanate or isothiocyanate (VIII) as set forth in the following reaction scheme:

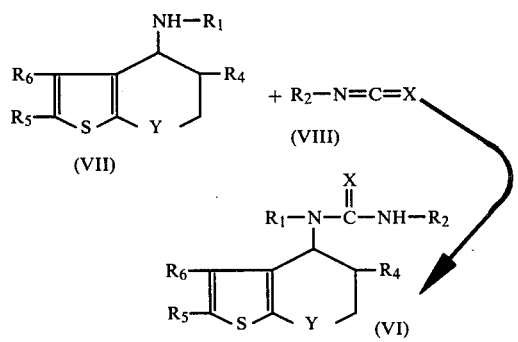

wherein X, Y, $R_1$, $R_2$, $R_4$, $R_5$ and $R_6$ are as hereinabove defined. The reaction can be carried out using approximately equimolar amounts of the isocyanate or isothiocyanate and the amine or amine acid salt; however, it is generally preferable to employ from 5% to 50% excess of the isocyanate or isothiocyanate wherein the tetrahydrobenzo ring does not contain a hydroxyl group. The reaction can be conducted at atmospheric or superatmospheric pressure at a temperature in the range of 0° C. to 100° C., but is preferably conducted at atmospheric pressure at 0° C. to 70° C. in the presence of an organic solvent. Suitable organic solvents include aprotic aromatic solvents such as benzene, toluene, and xylene; chlorinated hydrocarbon solvents such as methylene chloride, chloroform, and dichloroethane; ethers such as tetrahydrofuran, diethyl ether, dimethoxyethane, diethylene glycol dimethyl ether, and dioxane; lower alkyl $C_1$-$C_4$ ketones such as acetone, methyl ethyl ketone, methyl butyl ketone, and methyl isobutyl ketone, or mixtures of said solvents.

When the above reaction is carried out using a 4,5,6,7-tetrahydrobenzo[b]thiophen-4-amine acid salt, it is desirable to add an acid acceptor to the reaction mixture. Suitable acid acceptors include trialkylamines such as triethylamine, trimethylamine, pyridine or the like; alkali metal carbonates such as sodium and potassium carbonate; alkaline earth metal carbonates such as calcium carbonate; strong basic in exchange resins; and aqueous alkali in a 2-phase system using an immiscible hydrocarbon solvent such as benzene or toluene, or a chlorinated hydrocarbon such as chloroform or dichloroethane.

Formula (I) 4,5,6,7-tetrahydrobenzo[b]thien-4-yl-urea compounds wherein $R_2$ and $R_3$ are hydrogen may be advantageously prepared from the above-identified amine (VII) or its acid salt by reacting said amine with an approximately equimolar amount of sodium or potassium cyanate or thiocyanate. However, it is generally preferable to employ 5% to 50% excess of the cyanate or thiocyanate wherein the tetrahydrobenzo ring does not contain a hydroxy group. The reaction can be conducted under the conditions described above in detail. Suitable solvents include water, polar solvents such as $C_1$-$C_3$ alcohols, tetrahydrofuran, dioxane, ethyleneglycol dimethyl ether, diethylene glycol, dimethyl ether, acetone, methyl ethyl ketone and the like and mixtures thereof; in the pH range of 5 to 7 and preferably at pH 6.

Certain of the formula (I) b 4,5,6,7-tetrahydrobenzo[b]thien-4-ylurea compounds (XI) may be readily prepared by reacting approximately equimolar amounts of an appropriately substituted 4,5,6,7-tetrahydrobenzo[b]thien-4-yl isocyanate or isothiocyanate (IX) and an appropriately substituted $R_2R_3NH$ amine (X) or its acid-addition salt. The reaction can be graphically illustrated as follows:

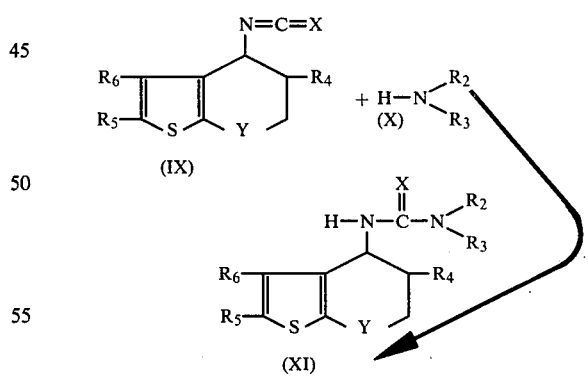

wherein X, Y, $R_2$, $R_3$, $R_4$, $R_5$ and $R_6$ are as hereinabove defined; with the proviso that Y is not —CHOH. In practice, the reaction is usually conducted with a slight excess (i.e. up to 20% excess) of the amine in the presence of a solvent, such as described above. Although the reaction may be conducted at superatmospheric pressure and temperatures as high as 100° C., it is generally preferable to conduct the reaction at atmospheric pressure at a temperature between 0° C. and 80° C. When a $R_2R_3NH$ amine acid salt is used it is most beneficial to introduce into the reaction mixture an acid acceptor such as described above. When an aqueous or a $C_1$–$C_3$ alcoholic ammonia or amine solution is used in the above reaction sequence, then the formula (XI) compounds are obtained wherein $R_2$ and $R_3$ are as defined above.

Preparation of the isocyanates (IX) utilized in the above reaction is readily accomplished by reacting the appropriate 4,5,6,7-tetrahydrobenzo[b]thiophen-4-amines or their acid salts with phosgene, preferably under anhydrous conditions and under a blanket of inert gas such as nitrogen. The reaction is initially carried out at a temperature between about 0° C. to 40° C., preferably 10° C. to 20° C., and then heated to between about 50° C. and 100° C., and preferably to from 60° C. to 80° C. The reaction is usually also conducted in the presence of an organic solvent such as benzene, toluene or xylene. The isothiocyanates (IX) can be prepared by reacting the appropriate 4,5,6,7-tetrahydrobenzo[b]thiophen-4-amines with equimolar amounts of carbon disulfide, triethylamine, and a carbodiimide represented by the formula: G—N=C=N—G where G is cyclohexyl, cycloheptyl, alkyl $C_4$-$C_8$ or the like. This reaction is generally conducted in the presence of a solvent such as tetrahydrofuran or an ether such as diethyl ether, at a temperature between about −10° C. and +25° C. The product can be isolated by distillation or by dry-column chromatography. Alternatively, the formula (IX) isothiocyanates can be prepared by the reaction of 1,1′-thiocarbonyldiimidazole with 4,5,6,7-tetrahydrobenzo[b]thiophen-4-amines in the presence of chloroform at ambient temperature.

The reaction of thiocarbonyl diimidazole in the above-mentioned reaction may also lead to the isolation of 1-(1-imidazolyl)-3-(4,5,6,7-tetrahydrobenzo[b]thien-4-yl)-thiourea. The analogous reaction also occurs when carbonyl diimidazole is used at room temperature and these reactions may be illustrated as follows:

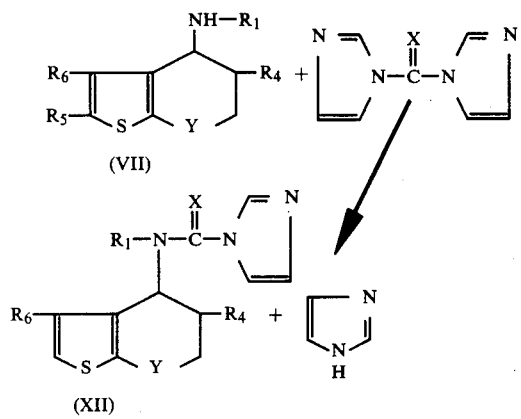

(VII)

(XII)

where $R_1$, $R_4$, $R_5$, $R_6$, Y and X are as previously defined. This intermediate (XII) has been discovered to be useful for preparing growth promoting urea compounds especially when the corresponding 4-isocyanate or 4-isothiocyanates of the benzothiophene-4-amines are difficult to prepare by conventional methods. The reaction may be illustrated as follows:

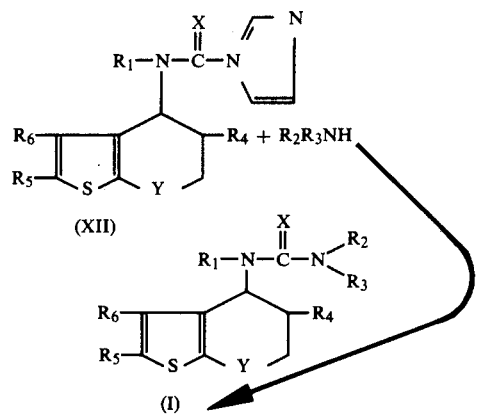

(XII)

(I)

The reaction is run at room temperature to 100° C. and preferably at 25°–50° C. in inert solvents such as chloroform, tetrahydrofuran, methylene chloride and the like.

Advantageously, formula (I) 4,5,6,7-tetrahydrobenzo[b]thien-4-ylurea compounds wherein Y is carbonyl (XIV) may be readily prepared from the corresponding formula (I) compounds wherein Y is methylene (XIII) by an oxidation reaction as set forth in the following reaction scheme:

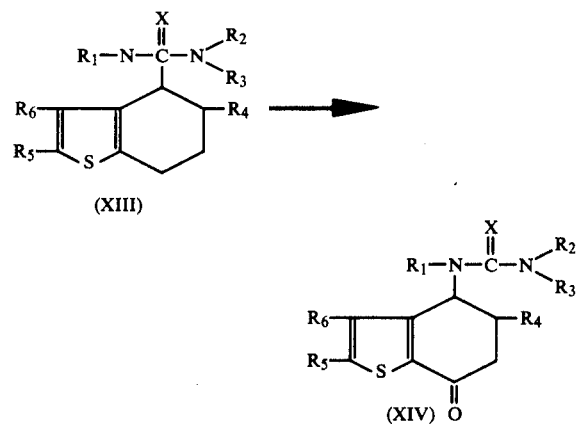

(XIII)

(XIV)

wherein X, $R_1$, $R_2$, $R_3$, $R_4$, $R_5$ and $R_6$ are as hereinabove defined with the proviso that $R_2$ cannot be hydroxyl, or a group containing hydroxyl, or —$SCH_3$, or an aryl—$CH_3$, or an aryl- or heteroaryl-methylene. The oxidation is carried out by treating a compound of formula (XIII) with a 2 to 8 mole equivalent and preferably with a 4 to 5 mole equivalent of an oxidizing agent selected from the group consisting of ceric ammonium nitrate, silver oxide, or sodium bichromate, at a temperature between about 0° C. and 100° C., and preferably 20° C. to 60° C., in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or the oxidizing agent chromic anhydride in acetic anhydride followed by hydrolysis.

Furthermore, formula (I) 4,5,6,7-tetrahydrobenzo[b]thien-4-ylurea compounds wherein Y is carbonyl (XVIII) can also be prepared by the above described oxidative process as set forth in the following reaction scheme:

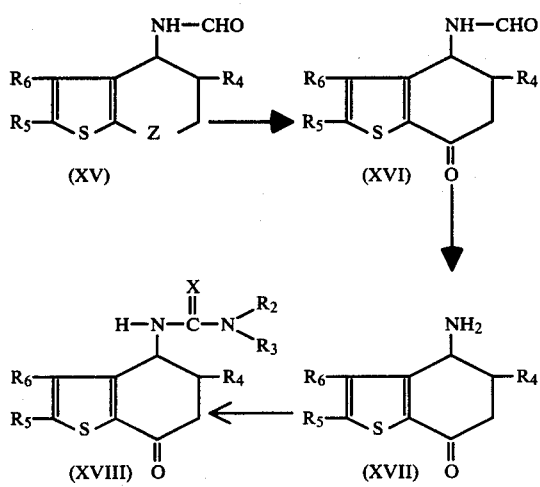

wherein Z is methylene or hydroxymethylene and X, R₂, R₃, R₄, R₅ and R₆ are as hereinabove defined. Upon completion of the oxidation step, the resulting 7-oxo compounds (XVI) are hydrolyzed in dilute mineral acid. The thus-obtained amine (XVII) acid-addition salts are then reacted with an isocyanate or an isothiocyanate at pH 5–7 as hereinbefore described in detail to yield the desired ureas or thioureas (XVIII).

The corresponding 7-hydroxy analogs are prepared from the corresponding formula (I) compounds wherein Y can be only carbonyl by reduction with equimolar or excess amounts of sodium borohydride, at a temperature range between about 0° C. and 75° C., preferably 20°–40° C., in $C_1$–$C_3$ alcohols to afford a mixture of the cis and trans isomers. All of the hereinabove described processes for the preparation of formula (I) 4,5,6,7-tetrahydrobenzo[b]thien-4-ylurea compounds yield racemic (dl) mixtures.

The novel compounds of the present invention may also be readily prepared by treating an appropriately substituted 4,5,6,7-tetrahydrobenzo[b]thiophen-4-amine (VII) with an appropriately substituted carbamoyl or thiocarbamoyl halide (XIX) as set forth in the following reaction scheme:

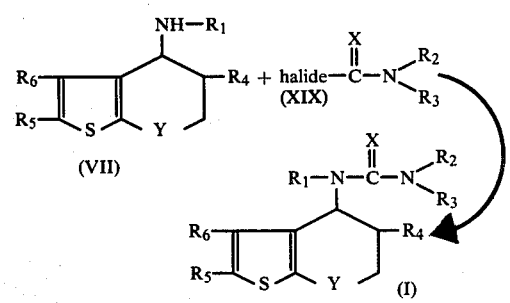

wherein R₁, R₂, R₃, R₄, R₅, R₆, X and Y are as hereinabove defined and halide may be chloro or bromo with the proviso that R₂ may not be hydroxyl, or a group containing hydroxyl, or a thioether. The free base of (VII) may be employed or an acid-addition salt thereof, preferably the hydrochloride, in the presence of an acid acceptor. Suitable acid acceptors may be pyridine, triethylamine (or any suitable tertiary amine), alkali metal carbonates such as potassium carbonate and sodium carbonate, strong basic ion-exchange resins, and aqueous alkali. The reaction may be run from about room temperature up to about 100° C. and preferably at 25°–50° C. until the desired reaction is complete. The reaction may be carried out under aqueous conditions or in any inert organic solvent such as tetrahydrofuran, dimethoxyethane, and even alcohols. The carbamoyl chloride or thiocarbamoyl chloride is generally used in equivalent amounts but it may be used in excess.

The preparation of the optically active 4,5,6,7-tetrahydrobenzo[b]thiophen-4-amine which is a useful intermediate for the synthesis of optically active 4,5,6,7-tetrahydrobenzo[b]thien-4-ylureas of formula (I) may be accomplished as follows. The racemic (dl) 4,5,6,7-tetrahydrobenzo[b]thiophen-4-amine is treated with the (+)-N-benzoylglutamic acid to form a water-insoluble salt of (+)-4,5,6,7-tetrahydrobenzo[b]thiophen-4-amine in high yield. It is not necessary to employ more than one mole of the resolving acid for each two moles of dl amine, as a cheaper acid, preferably acetic acid, can be substituted for the balance of required acid. In this way it is possible to obtain a high yield of the desired (+)-amine based on the resolving acid. The resolved salt, (+)-4,5,6,7-tetrahydrobenzo[b]thiophen-4-amine- .(+)-N-benzoylglutamic acid, is treated with alkali which liberates the (+)-amine which separates as an insoluble phase. It can be mechanically separated from the aqueous phase or extracted conventionally with a suitable solvent.

The (−)-amine which remains in solution is then recovered and treated with (−)-N-benzoylglutamic acid and acetic acid in the above-mentioned manner with the molarity adjusted to the amount of (+) amine obtained from the initial resolution. The salt, (−)-4,5,6,7-tetrahydrobenzo[b]thiophen-4-amine.(−)-N-benzoylglutamic acid, crystallizes and is then treated in the above-mentioned manner to give the (−)-amine.

With respect to optical isomers, the most preferred optically active ureido compounds for enhancement of growth in animals are those which are derived from the (+)-4,5,6,7-tetrahydrobenzo[b]thiophen-4-amine. For herbicidal activity, both (+)- and (−)-4,5,6,7-tetrahydrobenzo[b]thien-4-ylureas are desirable, since they both have pre-emergence activity against weeds. Thus, the following reaction schemes will exemplify the sequence in the preparation of the optically active compounds.

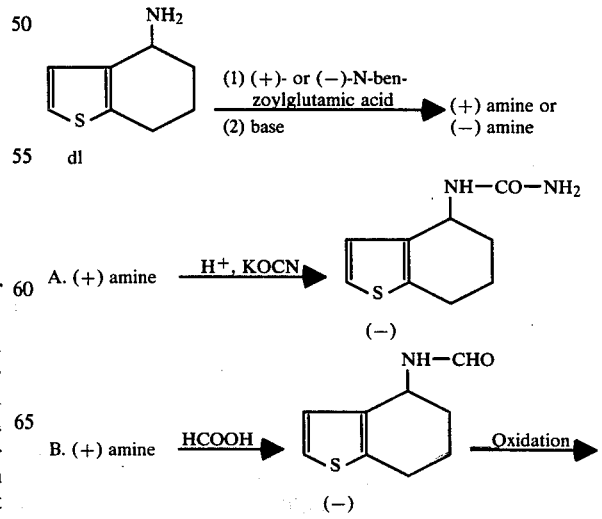

-continued

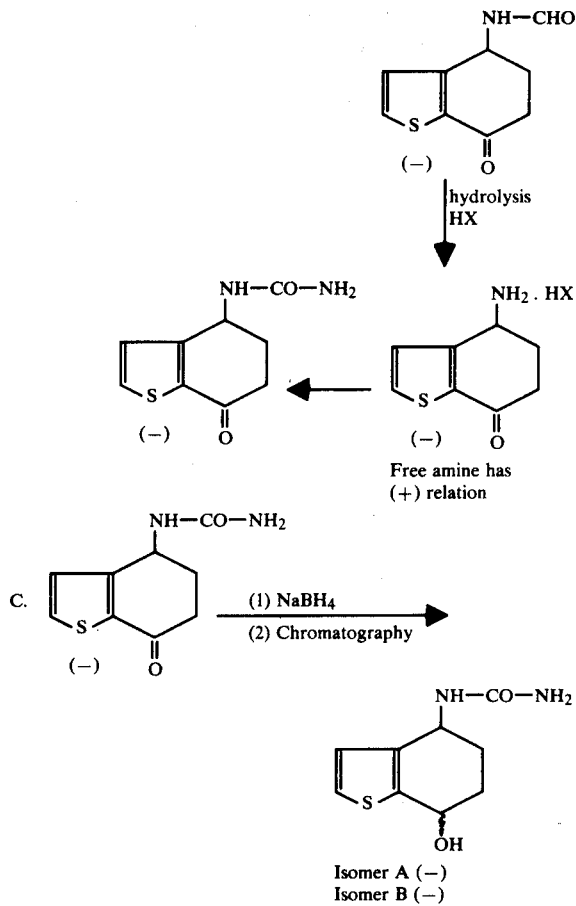

The separation of cis and trans-(−)-4,5,6,7-tetrahydro-7-hydroxybenzo[b]thien-4-ylureas is readily achieved by using preparative high-pressure liquid chromatography on silica gel with 1800 ml. of hexane/1000 ml. of CHCl₃/425 ml. of MeOH at a flowrate of 40 ml./minute. Since the configurations have not been established, the isomers are designated as Isomer A and Isomer B. Conversely, if (−)-4,5,6,7-tetrahydrobenzo[b]thiophen-4-amine is used in the above sequence, the resulting derivatives of the opposite sign are obtained.

Because 4,5,6,7-tetrahydro-7-oxobenzo[b]thiophen-4-amine is also a useful intermediate, this compound in its optically active form is desirable. Thus, dl-4,5,6,7-tetrahydro-7-oxobenzo[b]thiophen-4-amine is readily resolved with (+)-tartaric acid in methanol as follows:

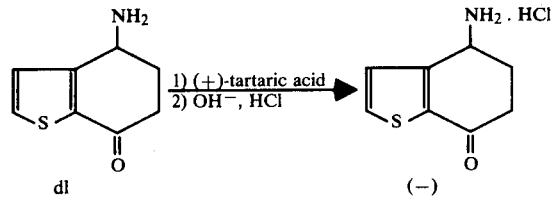

and the resulting crystalline tartrate salt is recrystallized from 95% ethanol. The salt is decomposed with aqueous NaOH solution and the optically active keto-amine is separated by conventional extraction and acidified with HCl to afford (−)-4,5,6,7-tetrahydro-7-oxobenzo[b]thiophen-4-amine hydrochloride, which can be used in the manner described above.

The compounds of this invention are useful as growth-promoting agents for animals such as poultry, fur-bearing and farm animals, and the use of said compounds for this purpose provides the added advantage of improving feed conversion for said animals. As used herein, the term "feed conversion" means the ratio of unit weight of feed per unit weight of gain and improvement in feed conversion means increased weight gain from a given unit of feed consumed.

In practice, a growth-promoting amount of a formula (I) 4,5,6,7-tetrahydrobenzo[b]thien-4-ylurea or an optically active isomer is administered to a host animal usually in, or with, the animal's feed. However, said compound may also be administered as a subcutaneous implant under the skin of said animal or as a parenteral injection. When administered in the feed of chickens, turkeys, sheep, cattle, goats, and the like, usually about 0.0001% to 0.08% by weight, and preferably 0.001% to 0.04% by weight of the formula (I) urea, is effective for increasing growth rate and improving feed conversion. When administered to said animals as a parenteral injection or subcutaneous implant, usually in amounts that will supply about 0.001 mg. to 0.20 mg. and preferably 0.005 mg. to 0.10 mg. per kg. of body weight per day of the active compound, will produce the desired improvement in weight gain and enhance food conversion. In tests conducted with day old chicks, it was found that from 1 ppm to 9 ppm of 4,5,6,7-tetrahydrobenzo[b]thien-4-ylurea administered in the chick feed produced a 3.3% to 6.6% improvement in weight gain over untreated controls, and likewise produced a 2.7% to 4.7% improvement in feed conversion.

The compounds of this invention are also useful as herbicidal agents. They are effective for controlling undesirable broadleaf and grass weeds when applied to soil containing seeds of said undesirable weeds, or when applied to the foliage of such plants. Usually about 5 pounds to 15 pounds, and preferably about 8 pounds to 10 pounds, per acre of the active compound is sufficient to provide control of the undesirable plants.

The present invention is further illustrated by the preparation of representative examples set forth below, as well as testing data on typical compounds of the invention.

EXAMPLE 1

Preparation of 1-methyl-3-(4,5,6,7-tetrahydrobenzo[b]thien-4-yl)urea

A mixture of 1.89 grams (0.01 mole) of 4,5,6,7-tetrahydrobenzo[b]thiophen-4-amine hydrochloride in 20 ml. of dry benzene is stirred while 1.05 grams (0.01 mole) of triethylamine and 01.7 ml. (excess) of methyl isocyanate are added successively. Addition of the latter gives rise to an exotherm, and the mixture becomes very pasty. The mixture is kept at 45° C. for one hour, and after cooling to room temperature, the solid is collected, washed thoroughly with benzene and then with water. On drying, this gives 1.7 grams (81%) of product, melting point 183° C. to 186° C. Recrystallization from acetone gives 1.23 grams, melting point 187.5° C. to 189° C.

On a 0.05 mole scale, the crude yield is 83% (9.15 grams), and the product melts at 181° C. to 186° C. Recrystallization from acetone gives 6.5 grams, melting point 184.5° C. to 187° C.

EXAMPLE 2

Preparation of 1-ethyl-3-(4,5,6,7-tetrahydrobenzo[b]thien-4-yl)urea

In the manner described in Example 1, ethyl isocyanate is allowed to react with 4,5,6,7-tetrahydrobenzo[b]thiophen-4-amine hydrochloride to afford 10.1 grams of 1-ethyl-3-(4,5,6,7-tetrahydrobenzo[b]thien-4-yl)urea. Recrystallization of the crude product from 2-propanol-water (9/1) affords crystals which are dissolved in chloroform and washed successively with 1 N sulfuric acid, water and saturated sodium bicarbonate solution. This gives the desired product, melting point 184° C. to 188.5° C. after evaporation of the chloroform.

EXAMPLE 3

Preparation of 1-isopropyl-3-(4,5,6,7-tetrahydrobenzo[b]thien-4-yl)urea

In a nitrogen atmosphere, 5.35 grams of 4,5,6,7-tetrahydrobenzo[b]thiophen-4-amine is stirred in 100 ml. of diethyl ether, and 3.57 grams of isopropyl isocyanate in 40 ml. of diethyl ether is slowly added to afford crystalline product. The mixture is stirred for an additional 0.5 hour and then filtered after standing overnight to give 8.3 grams, melting point 223° C. to 226° C., of 1-isopropyl-3-(4,5,6,7-tetrahydrobenzo[b]thien-4-yl)urea.

EXAMPLE 4

Preparation of 1-(n-hexyl)-3-(4,5,6,7-tetrahydrobenzo[b]thien-4-yl)urea

In the manner described in Example 1, 4,5,6,7-tetrahydrobenzo[b]thiophen-4-amine is allowed to react with n-hexyl isocyanate to give 1-(n-hexyl)-3-(4,5,6,7-tetrahydrobenzo[b]thien-4-yl)urea, melting point 122° C. to 124° C.

EXAMPLE 5

Preparation of 1-cyclohexyl-3-(4,5,6,7-tetrahydrobenzo[b]thien-4-yl)urea

In a similar manner, as described in Example 1, 4,5,6,7-tetrahydrobenzo[b]thiophen-4-amine hydrochloride is allowed to react with cyclohexyl isocyanate in dry tetrahydrofuran to afford 7 grams of 1-cyclohexyl-3-(4,5,6,7-tetrahydrobenzo[b]thien-4-yl)urea, melting point 222° C. to 225° C.

EXAMPLE 6

Preparation of 1-methoxy-3-(4,5,6,7-tetrahydrobenzo[b]thien-4-yl)urea

A mixture of 5 grams of methoxyamine hydrochloride in 60 ml. of methylene chloride is cooled to about 15° C., and 6 grams of triethylamine in 15 ml. of methylene chloride is added. After 20 minutes, 5.38 grams of 4,5,6,7-tetrahydrobenzo[b]thien-4-yl isocyanate in 20 ml. of methylene chloride is added over 20 minutes at 15° C. to 20° C. After stirring for an hour, the mixture is filtered, and the filtrate is washed with water and then aqueous sodium bicarbonate solution. The solution is dried and evaporated to afford a white solid. The solid is recrystallized from acetone-hexane to afford 5.1 grams, melting point 138.5° C. to 141° C., of 1-methoxy-3-(4,5,6,7-tetrahydrobenzo[b]thien-4-yl)urea.

Similarly, 1-ethoxy-3-(4,5,6,7-tetrahydrobenzo[b]thien-4-yl)urea and 1-butoxy-3-(4,5,6,7-tetrahydrobenzo[b]thien-4-yl)urea are prepared by using ethoxyamine hydrochloride and n-butoxyamine hydrochloride, respectively, in place of methoxyamine hydrochloride.

EXAMPLE 7

Preparation of 1-benzyloxy-3-(4,5,6,7-tetrahydrobenzo[b]thien-4-yl)urea

In the manner described in Example 6, O-benzyl hydroxyamine hydrochloride and 4,5,6,7-tetrahydrobenzo[b]thien-4-yl isocyanate are allowed to react to afford 1-(benzyloxy)-3-(4,5,6,7-tetrahydrobenzo[b]thien-4-yl)urea, which is recrystallized from 95% ethyl alcohol-methyl isobutyl ketone. The product melts at 96.5° C. to 99° C.

EXAMPLE 8

Preparation of 1-hydroxy-1-methyl-3-(4,5,6,7-tetrahydrobenzo[b]thien-4-yl)urea

In the manner described in Example 6, N-methylhydroxylamine hydrochloride and 4,5,6,7-tetrahydrobenzo[b]thien-4-yl isocyanate are allowed to react to afford 1-hydroxy-1-methyl-3-(4,5,6,7-tetrahydrobenzo[b]thien-4-yl)urea, which is recrystallized from acetone-hexane-ether to give crystals, with melting point 98° C. to 102° C.

EXAMPLE 9

Preparation of 1-methoxy-1-methyl-3-(4,5,6,7-tetrahydrobenzo[b]thien-4-yl)urea

Following the procedure described in Example 6, N,O-dimethyl hydroxylamine hydrochloride and 4,5,6,7-tetrahydrobenzo[b]thien-4-yl isocyanate are allowed to react to give 1-methoxy-1-methyl-3-(4,5,6,7-tetrahydrobenzo[b]thien-4-yl)urea, which is crystallized from acetone-hexane-ether to give product melting at 60° C. to 62.5° C.

EXAMPLE 10

Preparation of 4,5,6,7-tetrahydrobenzo[b]thien-4-ylurea

A mixture of 50 grams of 4,5,6,7-tetrahydrobenzo[b]thiophen-4-amine hydrochloride (about 45 grams real, based on 90% purity) in 100 ml. of water is stirred at about 15° C., and a solution of 23.1 grams of potassium cyanate in 100 ml. of water is added dropwise. After completion of the addition, the mixture is warmed slowly to 70° C. to 75° C. and held for an hour. The mixture is cooled, and the white solid is collected by filtration and washed with water. The solid is air-dried, pulverized, and washed with acetonitrile. On drying, this gives 37.3 grams of crude product, which on treatment with about 1200 ml. of hot acetone gives 11.45 grams, melting point 200° C. to 204° C. of the title compound.

Similarly, 2-methyl- and 3-methyl-4,5,6,7-tetrahydrobenzo[b]thien-4-ylurea are prepared to give products melting at 232°–233° C. and 227°–230° C. (dec.), respectively. When N-methyl-4,5,6,7-tetrahydrobenzo[b]thiophen-4-amine hydrochloride is used, 1-methyl-1-(4,5,6,7-tetrahydrobenzo[b]thien-4-yl)urea, melting point 151.5°–154.5° C., is obtained.

EXAMPLE 11

Preparation of
1-phenethyl-3-(4,5,6,7-tetrahydrobenzo[b]thien-4-yl)urea

A mixture of 3.82 grams of phenethylamine in 100 ml. of diethyl ether under nitrogen atmosphere is allowed to react with 5.38 grams of 4,5,6,7-tetrahydrobenzo[b]thien-4-yl isocyanate in 25 ml. of diethyl ether via dropwise addition of the latter solution. After stirring an hour at room temperature, the mixture is filtered and washed with ether to give 7.9 grams, melting point 163° C. to 166° C., of 1-phenethyl-3-(4,5,6,7-tetrahydrobenzo[b]thien-4-yl)urea.

In a similar manner, methylamine, ethylamine, isopropylamine, n-hexylamine and cyclohexylamine are allowed to react with the aforementioned isocyanate to afford 1-methyl-, 1-ethyl, 1-isopropyl-, n-hexyl- and 1-cyclohexyl-3-(4,5,6,7-tetrahydrobenzo[b]thien-4-ylurea.

EXAMPLE 12

Preparation of
1,1-dimethyl-3-(4,5,6,7-tetrahydrobenzo[b]thien-4-yl)urea

A solution of 6.27 grams of 4,5,6,7-tetrahydrobenzo[b]thien-4-yl isocyanate in 200 ml. of diethyl ether is charged with gaseous dimethylamine introduced via a capillary tube with stirring. After 0.5 hour of bubbling, the gas flow is terminated, and the mixture is evaporated to dryness to give a solid residue. This is crystallized from acetone-hexane-ether to give 1,1-dimethyl-3-(4,5,6,7-tetrahydrobenzo[b]thien-4-yl)urea melting at 117° C. to 120° C.

The identical product is obtained when 4,5,6,7-tetrahydrobenzo[b]thiophen-4-amine is allowed to react with equivalent amounts (or excess) of dimethylcarbamoyl chloride and triethylamine in dimethylformamide. The reaction mixture is stirred for several hours and then filtered. The filtrate is evaporated to dryness and the residue is purified by crystallization from acetone-hexane to afford the title compound.

EXAMPLE 13

Preparation of
1-benzyl-3-(4,5,6,7-tetrahydrobenzo[b]thien-4-yl)urea

In the manner described in Example 6, except for the use of diethyl ether instead of methylene chloride, 1-benzyl-3-(4,5,6,7-tetrahydrobenzo[b]thien-4-yl)urea is obtained by allowing benzylamine and 4,5,6,7-tetrahydrobenzo[b]thien-4-yl isocyanate to react. The product melts at 211° C. to 214° C.

The title compound is also obtained by allowing benzyl isocyanate to react with 4,5,6,7-tetrahydrobenzo[b]thiophen-4-amine in ether.

EXAMPLE 14

Preparation of
1-hydroxy-3-(4,5,6,7-tetrahydrobenzo[b]thien-4-yl)urea

The above compound is prepared in the manner described in Example 6, by allowing 4,5,6,7-tetrahydrobenzo[b]thien-4-yl isocyanate to react with hydroxylamine hydrochloride in the presence of triethylamine. The product melts at 158.5° C. to 160.5° C.

EXAMPLE 15

Preparation of
N-(4,5,6,7-tetrahydrobenzo[b]thien-4-yl)-4-morpholinecarboxamide

In the manner outlined in Example 6, except for using diethyl ether instead of methylene chloride, 4,5,6,7-tetrahydrobenzo[b]thien-4-yl isocyanate is allowed to react with morpholine to give N-(4,5,6,7-tetrahydrobenzo[b]thien-4-yl)-4-morpholinecarboxamide, which melts at 152° C. to 154° C.

EXAMPLE 16

Preparation of
2-bromo-4,5,6,7-tetrahydrobenzo[b]thien-4-ylurea

A sample of 7.84 grams of 4,5,6,7-tetrahydrobenzo[b]thien-4-ylurea is dissolved in 72 ml. of acetic acid, and 24 ml. of water is added. Bromine (2.3 ml. or 7.05 grams) in 32 ml. of acetic acid is added dropwise. The mixture is stirred at room temperature for 0.5 hour, and then 7.23 grams of sodium acetate in 40 ml. of water is added. An additional 120 ml. of water is added and stirring is continued for 0.5 hour. The white solid is collected, washed with water and cold sodium acetate solution to give 9.8 grams, melting point 206.5° C. to 209.5° C., of 2-bromo-4,5,6,7-tetrahydrobenzo[b]thien-4-ylurea.

EXAMPLE 17

Preparation of
2-bromo-N-formyl-4,5,6,7-tetrahydrobenzo[b]thiophen-4-amine

A sample of 54.3 grams of N-formyl-4,5,6,7-tetrahydrobenzo[b]thiophen-4-amine is stirred in 270 ml. of acetic acid and 90 ml. of water. Bromine (53 grams) in 120 ml. of acetic acid is added gradually. After stirring for 0.5 hour at room temperature, 61.5 grams of sodium acetate in 225 ml. water is added. More water is added, and the mixture is extracted with ether. Methylene chloride is added to the ether solution to prevent crystallization, and the solution is evaporated to dryness. The residue is crystallized from acetone-hexane-ether to afford 61 grams, melting point 104° C. to 108° C., of 2-bromo-N-formyl-4,5,6,7-tetrahydrobenzo[b]thiophen-4-amine.

EXAMPLE 18

Preparation of
2-cyano-N-formyl-4,5,6,7-tetrahydrobenzo[b]thiophen-4-amine

A mixture of 40.9 grams of 2-bromo-N-formyl-4,5,6,7-tetrahydrobenzo[b]thiophen-4-amine, 16.2 grams of cuprous cyanide and 47 ml. of dry dimethylformamide is heated at reflux temperature for 4 hours, and then cooled to about 60° C. and poured into 270 ml. of water. The mixture is extracted with toluene several times, and the toluene extracts are washed with 1.2 N hydrochloric acid and saturated sodium chloride respectively. On drying, 5.7 grams of crude product is obtained. The aqueous mother liquor is treated with 97.3 grams of ferric chloride hexahydrate and 30 ml. of concentrated hydrochloric acid and shaken. It is then extracted with toluene several times, and the extracts are washed further with 1.2 N hydrochloric acid, saturated sodium bicarbonate solution and brine, respectively. On drying and evaporation of toluene, an additional 2.5 grams of product is obtained. The two crops are combined and recrystallized from acetone-hexane to afford 4.8 grams of 2-cyano-N-formyl-4,5,6,7-tetrahydrobenzo[b]thiophen-4-amine, melting point 131° C. to 134° C.

EXAMPLE 19

Preparation of 2-cyano-4,5,6,7-tetrahydrobenzo[b]thiophen-4-amine hydrochloride

A mixture of 4.8 grams of 2-cyano-N-formyl-4,5,6,7-tetrahydrobenzo[b]thiophen-4-amine in 70 ml. of 1 N hydrochloric acid is refluxed for an hour and evaporated to dryness to afford 4.7 grams of 2-cyano-4,5,6,7-tetrahydrobenzo[b]thiophen-4-amine hydrochloride, melting point 241° C. to 246° C. (dec.).

EXAMPLE 20

Preparation of 2-cyano-4,5,6,7-tetrahydrobenzo[b]thien-4-ylurea

The desired product, 2-cyano-4,5,6,7-tetrahydrobenzo[b]thien-4-ylurea, is prepared in the manner described in Example 10 by allowing 2-cyano-4,5,6,7-tetrahydrobenzo[b]thiophen-4-amine hydrochloride to react with potassium cyanate. The crude product melts at 210° C. to 214° C., and the product which is recrystallized from nitromethane melts at 209° C. to 213° C.

EXAMPLE 21

Preparation of 2-chloro-4,5,6,7-tetrahydrobenzo[b]thiophen-4-amine

A sample of 11.4 grams 4,5,6,7-tetrahydrobenzo[b]thiophen-4-amine hydrochloride is stirred in 150 ml. of chloroform at about 10° C., and 6.1 ml. of sulfuryl chloride is added dropwise. The mixture is stirred for 3.5 hours at room temperature, and then about 20 ml. of 50% sodium hydroxide solution is added gradually to dissolve the suspended solid. The mixture is then poured into water and extracted with chloroform twice. The extracts are dried, evaporated to dryness, and the residue is distilled to give 7.4 grams of 2-chloro-4,5,6,7-tetrahydrobenzo[b]thiophen-4-amine, boiling point 94° C. to 98° C./0.5 Torr.

EXAMPLE 22

Preparation of 2-chloro-4,5,6,7-tetrahydrobenzo[b]thien-4-ylurea

The desired product, 2-chloro-4,5,6,7-tetrahydrobenzo[b]thien-4-ylurea, is prepared in the manner described in Example 31 by allowing 2-chloro-4,5,6,7-tetrahydrobenzo[b]thiophen-4-amine to react with hydrocyanic acid in situ. The product melts at 194° C. to 198° C.

EXAMPLE 23

Preparation of N-(2-acetyl-4,5,6,7-tetrahydrobenzo[b]thien-4-yl)acetamide

N-acetyl-4,5,6,7-tetrahydrobenzo[b]thiophen-4-amine (19.5 grams) is stirred in 300 ml. of methylene chloride in a nitrogen atmosphere, and 17 ml. of acetyl chloride is added. The mixture is cooled to about 10° C., and 28.1 ml. of stannic chloride is added slowly. After stirring for 1.5 hours at room temperature, the mixture is cooled to about 10° C., and 450 ml. of 1.2 N hydrochloric acid is added. The mixture is shaken, and the methylene chloride solution is separated and washed with 1 N hydrochloric acid, followed by saturated sodium bicarbonate solution. On drying and evaporating to dryness, crystals are obtained. Recrystallization from acetone-hexane gives 15.4 grams, melting point 167.5° C. to 172° C., of N-(2-acetyl-4,5,6,7-tetrahydrobenzo[b]thien-4-yl)acetamide.

EXAMPLE 24

Preparation of 2-acetyl-4,5,6,7-tetrahydrobenzo[b]thiophen-4-amine hydrochloride The product from Example 23 (7.25 grams) is heated with 90 ml. of 1 N hydrochloric acid at reflux temperature for 8.5 hours and cooled. The mixture is diluted with water and extracted with methylene chloride. The aqueous layer is then evaporated to dryness using 2-propanol for facilitating removal of water. This gives 4.85 grams of 2-acetyl-4,5,6,7-tetrahydrobenzo[b]thiophen-4-amine hydrochloride.

EXAMPLE 25

Preparation of 2-acetyl-4,5,6,7-tetrahydrobenzo[b]thien-4-ylurea

A sample of 6.3 grams of 2-acetyl-4,5,6,7-tetrahydrobenzo[b]thiophen-4-amine hydrochloride is dissolved in 35 ml. of water and cooled to 15° C. A solution of 2.64 grams of potassium cyanate in 35 ml. of water is added, and after 0.5 hour the mixture is heated at 70° C. for about 40 minutes. The mixture is cooled, and the solid is collected and washed with water. On drying, 5.55 grams, melting point 218° C. to 220° C., of 2-acetyl-4,5,6,7-tetrahydrobenzo[b]thien-4-ylurea is obtained.

EXAMPLE 26

Preparation of 1-ethyl-3-(4,5,6,7-tetrahydrobenzo[b]thien-4-yl)thiourea

A sample of 9.48 grams of 4,5,6,7-tetrahydrobenzo[b]thiophen-4-amine hydrochloride is stirred in 100 ml. of dry tetrahydrofuran, and 6.06 grams of triethylamine is added. After stirring for 15 to 30 minutes, 5.23 grams of ethyl isothiocyanate in 20 ml. of dry tetrahydrofuran is added dropwise, and the mixture is heated for 2 hours at 50° C. The mixture is cooled and filtered, and the filter cake is washed with hexane. The filtrate is evaporated to dryness and poured on ice. The oil is extracted with ether, and the extract is washed with 1 N sulfuric acid, water, and saturated sodium bicarbonate solution. The ether extract is dried and evaporated to dryness to afford an oil. This oil crystallizes in ether to afford 1-ethyl-3-(4,5,6,7-tetrahydrobenzo[b]thien-4-yl)thiourea, melting point 106° C. to 112° C.

Similarly, use of methyl isothiocyanate, butyl isothiocyanate and cyclohexyl isothiocyanate affords 1-methyl-, 1-butyl- and 1-cyclohexyl-3-(4,5,6,7-tetrahydrobenzo[b]thien-4-yl)thioureas.

EXAMPLE 27

Preparation of 4,5,6,7-tetrahydrobenzo[b]thiophen-4-amine

A sample (61.2 grams) of 4,5,6,7-tetrahydrobenzo[b]thiophen-4-amine hydrochloride is suspended in 150 ml. of water, and about 400 ml. of 10% aqueous ammonium hydroxide is added to the mixture. The alkaline mixture is then extracted twice with ether, and after drying the ethereal solution is evaporated to dryness. The amine is then distilled to give 40.9 grams, boiling point 100° C. to 102° C. at 3 Torr., of 4,5,6,7-tetrahydrobenzo[b]thiophen-4-amine.

EXAMPLE 28

Preparation of
(−)-4,5,6,7-tetrahydrobenzo[b]thiophen-4-ammonium
(R)-N-benzoyl glutamate A mixture of 8.04 grams of (R)-(+)-N-benzoyl glutamic acid in 1.92 grams of acetic acid and 80 ml. of water is heated on a steam bath until a solution is obtained. This hot solution is stirred while 9.80 grams of 4,5,6,7-tetrahydrobenzo[b]thiophen-4-amine is added gradually. About 2 ml. of ethanol is used in the transfer as a rinse for the amine. The mixture is then allowed to cool to room temperature and to stand overnight. The mixture is cooled in a refrigerator, filtered to collect the crystals, and the filter cake is washed with water several times. On drying, this gives 9.27 grams of the title salt, melting point 192° C. to 194° C.; $[\alpha]_{589}^{25}$ −9.39°, $[\alpha]_{436}$ −44.6°, $[\alpha]_{365}$ −71.4° at c=4.475 in acetic acid.

The original filtrate is concentrated under reduced pressure to a small volume and partitioned between diethyl ether and aqueous sodium hydroxide. The aqueous base is extracted with ether, and this ether extract is combined with the first ether fraction. This is then dried over magnesium sulfate, evaporated to dryness to afford the recovered amine, and the amine is added to a stirred, hot solution of 8.04 grams of (S)-(−)-N-benzoyl glutamic acid in 1.92 grams of acetic acid and 80 ml. of water. Crystallization occurs rapidly, and after 10 minutes of heating on a steam bath, the mixture is allowed to cool in a refrigerator. The crystals are collected, washed with water and dried to afford 11.1 grams of (+)-4,5,6,7-tetrahydrobenzo[b]thiophen-4-ammonium (S)-N-benzoyl glutamate salt, melting point 192° C. to 193.5° C.; $[\alpha]_{589}^{25}$ +12.2°, $[\alpha]_{436}$ +42.7°, $[\alpha]_{365}$ +82° at c=4.35 in acetic acid.

EXAMPLE 29

Preparation of (−)
4,5,6,7-tetrahydrobenzo[b]thien-4-ylurea

The salt (8.8 grams of (−)-4,5,6,7-tetrahydrobenzo[b]thiophen-4-amine and (R)-(+)-N-benzoyl glutamic acid is added to ice water mixture in a separatory funnel, and 3.5 grams of sodium hydroxide in 55 ml. of water is added. The mixture is shaken until a solution is obtained, and then is extracted with diethyl ether twice. The ether extracts are washed with saturated sodium chloride solution, and with ice added the mixture is extracted with 2.36 ml. of concentrated hydrochloric acid in 25 ml. of water. The acid layer is then treated with 2.29 grams of potassium cyanate in 30 ml. of water at 20° C. After stirring for an hour, the mixture is heated to 0.5 hour and cooled. The product is collected by filtration, washed with water, and dried to give 2.75 grams, melting point 218.5° C. to 221.5° C.; $[\alpha]_{589}^{25}$ −63.2°, $[\alpha]_{436}$ −149.9°, $[\alpha]_{365}$ −271.5°, of (−)-4,5,6,7-tetrahydrobenzo[b]thien-4-ylurea.

Similarly, the salt of (+)-4,5,6,7-tetrahydrobenzo[b]thiophen-4-amine and (S)-(−)-N-benzoyl glutamic acid is treated in the above manner to afford (+)-4,5,6,7-tetrahydrobenzo[b]thien-4-ylurea, melting point 218° C. to 220° C.; $[\alpha]_{589}^{25}$ +60°, $[\alpha]_{436}$ +149.8°, $[\alpha]_{365}$ +272.5°.

EXAMPLE 30

Preparation of 4,5,6,7-tetrahydrobenzo[b]thien-4-yl
isocyanate

A sample of 47.6 grams of 4,5,6,7-tetrahydrobenzo[b]thiophen-4-amine hydrochloride is stirred in 150 ml. of water, and 350 ml. of 10% sodium hydroxide is added. The mixture is shaken and extracted with benzene twice. The extract is dried and evaporated to dryness to afford the amine, which is stored under nitrogen. The amine is then added dropwise to 866 ml. of 12.5% phosgene solution (benzene) in nitrogen atmosphere at 20° C. After stirring for an hour at room temperature, the mixture is gradually heated to 60° C. and kept at this temperature for 7 hours. The mixture is cooled to room temperature and evaporated to dryness to afford a residue, which is distilled to give 22.4 grams, boiling point 98° C. to 101° C./0.6 Torr., of 4,5,6,7-tetrahydrobenzo[b]thien-4-yl isocyanate.

EXAMPLE 31

Preparation of 4,5,6,7-tetrahydrobenzo[b]thien-4-ylurea

A sample of 4,5,6,7-tetrahydrobenzo[b]thiophen-4-amine (19.9 grams) is cooled in a flask, and a solution of 12 ml. of 12 N hydrochloric acid in 50 ml. of water is slowly added. Subsequently, at about 20° C., a solution of 11.7 grams of potassium cyanate in 80 ml. of water is added in 0.5 hour. The mixture is stirred at room temperature for one hour and then warmed to 60° C. and kept at this temperature for 0.5 hour. After standing overnight at room temperature, the product is collected and washed with water to afford 21 grams, melting point 206° C. to 209° C.

EXAMPLE 32

Mouse Growth Regulant Tests

CFI female mice from Carworth Farms are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the following tables. Twelve days later the mice are weighed again and the experiment terminated. At least three cages (30 mice) of untreated controls are included in each test. Test data are provided in Tables VI, VII, and VIII below wherein data are reported as percent weight gain over controls. Unless otherwise indicated in these tables, all compounds tested were dl-racemic mixtures. The following is a description of the diet to which the growth promoting compounds were added.

| DIET | |
|---|---|
| GUARANTEED ANALYSIS | |
| Crude protein not less than | 23.0% |
| Crude fat not less than | 4.5% |
| Crude fiber not more than | 6.0% |
| Ash not more than | 9.0% |
| INGREDIENTS | |
| Meat and bone meal, dried skimmed milk, wheat germ meal, fish meal, animal liver meal, dried beet pulp, ground extruded corn, ground oat | |

-continued

| DIET |
|---|
| groats, soybean meal, dehydrated alfalfa meal, cane molasses, animal fat preserved with BHA, vitamin B$_{12}$ supplement, calcium pantothenate, choline chloride, folic acid, riboflavin supplement, brewers' dried yeast, thiamin, niacin, |

-continued

| DIET |
|---|
| vitamin A supplement, D activated plant sterol, vitain E supplement, calcium carbonate, dicalcium phosphate, iodized salt, ferric ammonium citrate, iron oxide, manganous oxide, cobalt carbonate, copper oxide, zinc oxide. |

TABLE VI

Effectiveness of 4,5,6,7-Tetrahydrobenzo[b]thien-4-ylureas as Animal Growth Promoting Agents Reported as Percent Weight Gain Over Controls Using Mice as the Test Animal

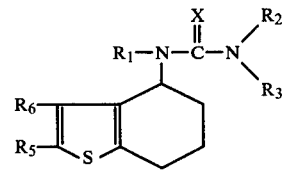

| Rate ppm in Diet | X | R$_5$ | R$_6$ | R$_1$ | R$_3$ | R$_2$ | % Weight Gain Over Controls |
|---|---|---|---|---|---|---|---|
| 50 | O | H | H | H | H | H | 50.1 |
| 400 | O | H | H | H | H | H | 119.6 |
| 50 | O | H | H | H | H | —CH$_3$ | 61.8 |
| 200 | O | H | H | H | H | H | 134.2 |
| 50 | O | H | H | H | H | —C$_2$H$_5$ | 40.3 |
| 200 | O | H | H | H | H | —C$_2$H$_5$ | 87.6 |
| 400 | O | H | H | H | —CH$_3$ | —OH | 49.6 |
| 400 | O | H | H | H | H | —OCH$_3$ | 68.6 |
| 400 | O | H | H | H | —CH$_3$ | —CH$_3$ | 55.1 |
| 400 | O | H | H | H | —CH$_3$ | —OCH$_3$ | 106.8 |
| 400 | O | H | H | H | H | —(CH$_3$)$_2$ | 88.0 |
| 400 | O | Br | H | H | H | H | 76.3 |
| 400 | O | Cl | H | H | H | H | 4.8 |
| 400 | O | H | H | —CH$_3$ | H | H | 27.2 |
| 400 | S | —CH$_3$ | H | H | —CH$_3$ | H | 88.5 |
| 400 | O | H | H | H | H (levorotatory enantiomorph) | H | 122.5 |
| 400 | O | H | H | H | H | —CH$_3$ | 134 |
| 400 | O | H | H | H | H | —C$_2$H$_5$ | 87.6 |
| 400 | O | H | H | H | H | n-hexyl | 14.5 |
| 400 | O | H | H | H | H | —CH$_2$C$_6$H$_5$ | 32.4 |
| 400 | O | H | H | H | H | —CH$_2$CH$_2$C$_6$H$_5$ | 72.3 |
| 400 | S | H | H | H | H | —C$_2$H$_5$ | 54.6 |
| 400 | O | H | H | H | —CH$_2$—CH$_2$—O—CH$_2$—CH$_2$— | | 9.9 |
| 400 | O | H | H | H | H | —CH$_2$—CH=CH$_2$ | 48.4 |
| 400 | O | H | H | H | H | ![tetrahydrobenzothiophene] | 43 |
| 400 | O | H | H | H | —CH$_2$—CH$_2$—CH$_2$—CH$_2$— | | 18 |
| 400 | O | H | H | H | -n-butyl | -n-butyl | 6 |
| 400 | S | H | H | H | H | H | 11 |
| 400 | S | H | H | H | H | —CH$_2$—CH$_2$—(2-pyridyl) | 15 |
| 400 | S | H | H | H | H | -n-butyl | 75 |
| 400 | O | H | H | H | H | —CH$_2$—CH$_2$—OH | 3 |
| 400 | S | H | H | H | H | -n-C$_8$H$_{17}$ | 16 |
| 400 | S | H | H | H | H | cyclopropyl | 32 |
| 400 | S | H | H | H | H | —CH$_2$—CH=CH | 60 |
| 400 | O | H | H | H | H | —CH$_2$—C≡CH | 82 |
| 400 | O | H | H | H | H | (tetrahydronaphthyl) | 4 |
| 400 | O | H | H | H | H | —CN | 1 |

TABLE VI-continued

Effectiveness of 4,5,6,7-Tetrahydrobenzo[b]thien-4-ylureas as Animal Growth Promoting Agents Reported as Percent Weight Gain Over Controls Using Mice as the Test Animal

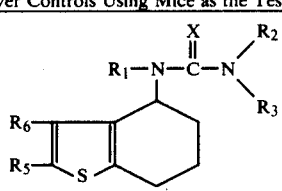

| Rate ppm in Diet | X | $R_5$ | $R_6$ | $R_1$ | $R_3$ | $R_2$ | % Weight Gain Over Controls |
|---|---|---|---|---|---|---|---|
| 400 | O | H | H | H | H | 2-bromo-5-methylphenyl | 1 |
| 400 | O | H | H | H | H | 2-methylindanyl | 8 |
| 200 | O | H | H | H | H | -n-butyl | 25 |
| 400 | O | H | H | H | H | —CH$_2$—O—CH$_3$ | 102 |
| 400 | O | H | H | H | H | —CH$_2$CN | 12 |
| 400 | O | H | H | H | —(CH$_2$)$_2$— | —(CH$_2$)$_2$— (piperazine ring with C=CH, HN, N—C$_6$H$_5$) | 14 |
| 400 | O | H | H | H | H | 2,4-dichlorophenyl | 18 |
| 400 | O | H | H | H | —CH$_3$ | —CH$_2$C≡CH | 29 |
| 400 | O | H | H | H | H | —NH—CO$_2$CH$_3$ | 18 |
| 400 | O | H | H | H | H | —CH$_2$—NH—CO—NH—(4,5,6,7-tetrahydrobenzo[b]thien-4-yl) | 29 |
| 400 | O | H | H | H | H | 4-methoxyphenyl | 78 |
| 400 | O | H | H | H | —CH$_2$—CH=CH$_2$ | —CH$_2$—CH=CH$_2$ | 4.0 |
| 400 | O | H | H | H | H | —CH$_2$-(2-thienyl) | 39 |
| 400 | O | H | H | H | —CH$_2$—C≡CH | —CH$_2$—C≡CH | 27 |
| 400 | O | H | H | H | H | —CH$_2$-(3-pyridyl) | 48 |
| 400 | O | H | H | H | H | —CH$_2$-(1-methylpyridinium iodide) | 6 |
| 400 | O | H | H | H | H | 4-chlorophenyl | 21 |

TABLE VI-continued

Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | X | $R_5$ | $R_6$ | $R_1$ | $R_3$ | $R_2$ | % Weight Gain Over Controls |
|---|---|---|---|---|---|---|---|
| 400 | O | H | H | H | H | $-CH_2-C_6H_4-OCH_3$ (para) | 16 |
| 400 | O | H | H | H | H | $-CH_2-$(2-pyridyl) | 41 |
| 400 | O | H | H | H | H | $-CH_2-$(4-pyridyl) | 46 |
| 400 | O | H | H | H | \multicolumn{2}{l|}{$-(CH_2)_2-\overset{H}{N}-(CH_2)_2-$} | 3 |
| 400 | O | H | H | H | H | $-CH_2CF_3$ | 19 |
| 400 | O | H | H | H | H | $-CH_2-C_6H_4-Cl$ (para) | 1 |
| 400 | O | H | H | H | H | $-(CH_2)_3-C_6H_4-CH_3$ (ortho) | 4 |
| 400 | O | H | H | H | $-CH_3$ | $-CH_2C_6H_5$ | 14 |
| 400 | O | H | H | H | H | $-CH_2-CH(OCH_3)_2$ | 22 |
| 400 | O | H | H | H | H | cyclopropyl | 31 |
| 400 | O | H | H | H | H | 2-thiazolyl | 11 |
| 400 | O | H | H | H | $-CH_2C_6H_5$ | $-CH_2-C\equiv CH$ | 30 |
| 400 | O | H | H | H | \multicolumn{2}{l|}{$-(CH_2)_2-N(C_6H_4-OCH_3)-(CH_2)_2-$} | 24 |
| 400 | O | H | H | H | \multicolumn{2}{l|}{$-(CH_2)_2-C_6H_4-CH_2-$ (ortho-fused)} | 7 |
| 400 | O | H | H | H | H | $-C_6H_4-NO_2$ (para) | 9 |
| 400 | O | H | H | H | H | 2,6-dimethylphenyl | 4 |

TABLE VI-continued

Effectiveness of 4,5,6,7-Tetrahydrobenzo[b]thien-4-ylureas as
Animal Growth Promoting Agents Reported as Percent Weight
Gain Over Controls Using Mice as the Test Animal

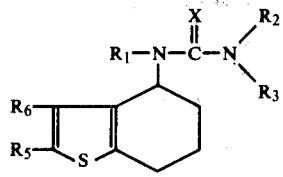

| Rate ppm in Diet | X | $R_5$ | $R_6$ | $R_1$ | $R_3$ | $R_2$ | % Weight Gain Over Controls |
|---|---|---|---|---|---|---|---|
| 400 | O | H | H | H | H | ![p-ethoxyphenyl]—⟨⟩—OC$_2$H$_5$ | 8 |
| 400 | O | H | H | H | H | ![p-n-butoxyphenyl]—⟨⟩—O-n-C$_4$H$_9$ | 9 |
| 400 | O | H | H | H | H | —OH | 102.9 |
| 400 | O | H | H | H | H | —OCH$_2$C$_6$H$_5$ | 7.8 |
| 400 | S | H | H | H | —CH$_3$ | —OCH$_3$ | 66 |
| 400 | O | H | H | H | H | —OC$_2$H$_5$ | 61 |
| 400 | O | H | H | H | H | —O—CH$_2$—CH=CH$_2$ | 5 |
| 400 | O | H | H | H | cyclohexyl | —OH | 19 |
| 400 | O | H | H | H | H | —O-n-C$_{16}$H$_{13}$ | 29 |
| 400 | O | H | H | H | —CH(CH$_3$)$_2$ | —OH | 32 |
| 400 | O | H | H | H | —CH$_2$C$_6$H$_5$ | —OH | 12 |
| 400 | O | —CH$_3$ | H | H | -2-butyl | H | 2 |
| 400 | O | H | —CH$_3$ | H | H | H | 26 |
| 400 | O | H | —CH$_3$ | H | H | -n-hexyl | 21 |
| 400 | O | —CH$_3$ | —CH$_3$ | H | -2-butyl | H | 3 |
| 400 | O | —CH$_3$ | —CH$_3$ | H | H | H | 0 |
| 400 | O | —NO$_2$ | H | H | H | H | 17 |
| 400 | O | H | H | H | H | —C(O)—CH$_3$ | −1.4 |
| 400 | S | H | H | H | H | —CO$_2$C$_2$H$_5$ | 22.3 |
| 400 | O | H | H | H | H | 2,4-dimethoxyphenyl (—⟨⟩(OCH$_3$)$_2$) | 32.4 |
| 400 | O | H | H | H | H | 3-methoxyphenyl (—⟨⟩—OCH$_3$) | 25.0 |
| 400 | O | H | H | H | H | —N(CH$_3$)$_2$ | 3.0 |
| 200 | O | H | H | H | H | —C(O)—CCl$_3$ | 37.4 |
| 400 | S | H | H | H | H | 4-methoxyphenyl (—⟨⟩—OCH$_3$) | −1.4 |
| 400 | O | H | H | H | H | —O-phenyl | 90.6 |
| 400 | O | H | H | H | H | —OCH$_2$—CO$_2$H | 63.3 |
| 400 | | | | | 1-methyl-3-(4-methyl-4,5,6,7-tetrahydrobenzo[b]-thien-4-yl)urea | | 39 |
| 400 | | | | | 1-methyl-3-(7,7-dimethyl-4,5,6,7-tetrahydrobenzo- | | |

TABLE VI-continued

Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | X | $R_5$ | $R_6$ | $R_1$ | $R_3$ | $R_2$ | % Weight Gain Over Controls |
|---|---|---|---|---|---|---|---|
| [b]thien-4-yl)urea | | | | | | | |

TABLE VII

Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | X | $R_3$ | $R_2$ | % Weight Gain Over Controls |
|---|---|---|---|---|
| 400 | O | H | —$CH_3$ | 64.8 |
| 400 | O | H | —$CH_2$—CH=$CH_2$ | 58.7 |
| 400 | O | H | —$C_2H_5$ | 79.3 |
| 200 | O | H | —$OCH_3$ | 71.0 |
| 200 | O | H | -iso-$C_3H_7$ | 84.0 |
| 200 | O | —$CH_3$ | —$CH_3$ | 58.6 |
| 200 | O | H | —$CH_2$—C≡CH | 40.6 |
| 200 | O | —$CH_3$ | —$OCH_3$ | 62.6 |
| 200 | O | —$CH_3$ | —OH | 31.3 |
| 400 | O | H | —C(O)—$CCl_3$ | 62.2 |

TABLE VII-continued

Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | X | $R_3$ | $R_2$ | % Weight Gain Over Controls |
|---|---|---|---|---|
| 400 | S | H | —$CH_3$ | 62.5 |
| 200 | O | H | H | 9.4 |
| (dextrorotatory enantiomorph) | | | | |
| 25 | O | H | H | 118.6 |
| (levorotatory enantiomorph) | | | | |
| 400 | O | H | -n-$C_8H_{17}$ | 83.4 |
| 400 | 2-bromo-4,5,6,7-tetrahydro-7-oxo benzo[b]thien-4-ylurea | | | 35.9 |
| 400 | O | H | n-$C_{10}H_{21}$ | 15.4 |
| 400 | O | H | n-$C_{12}H_{25}$ | 4.1 |
| 400 | O | H | n-$C_{14}H_{29}$ | 9.7 |

TABLE VIII

Effectiveness of 4,5,6,7-Tetrahydrobenzo[b]thien-4-ylureas as Animal Growth Promoting Agents Reported as Percent Weight Gain Over Controls Using Mice as the Test Animal

| Rate ppm in Diet | $R_3$ | $R_2$ | % Weight Gain Over Controls |
|---|---|---|---|
| 400 | H | —$CH_2$—CH=$CH_2$ | 29.1 |
| 200 | H | -iso-$C_3H_7$ | 43.9 |
| 400 | —$CH_3$ | —$CH_3$ | 81.5 |
| 400 | H | —$CH_3$ | 60.2 |
| 50 | H | —$CH_2$—C≡CH | 49.2 |
| 200 | —$CH_3$ | —$OCH_3$ | 60.5 |
| 200 | H | —$C_2H_5$ | 73.4 |
| 400 | H | —$OCH_3$ | 66.7 |
| 50 | H | H | −11.3 |
| (dextrorotatory diastereomer, 95% isomer B) | | | |
| 25 | H | H | 74.5 |
| (levorotatory diastereomer, 91.5% isomer B) | | | |
| 25 | H | H | 54.4 |
| (levorotatory diastereomer, 86% isomer A) | | | |
| 200 | H | H | 13.5 |
| (mixture of dextrorotatory disastereometers, 62% isomer B) | | | |

TABLE VIII-continued

Effectiveness of 4,5,6,7-Tetrahydrobenzo[b]thien-4-ylureas as Animal Growth Promoting Agents Reported as Percent Weight Gain Over Controls Using Mice as the Test Animal

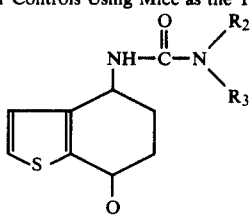

| Rate ppm in Diet | $R_3$ | $R_2$ | % Weight Gain Over Controls |
|---|---|---|---|
| 25 | H (dextrorotatory diastereomer, 90% isomer A) | H | 3.7 |
| 400 | 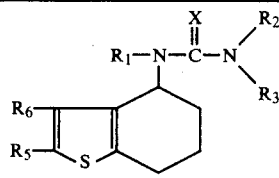 NH—CONH$_2$ | dl-cis (Isomer A) | 110 |
| 400 | | dl-trans (Isomer B) | 99 |

EXAMPLE 33

Preparation of 4,5,6,7-tetrahydrobenzo[b]thien-4-yl isothiocyanate

A sample (47.5 grams) of 4,5,6,7-tetrahydrobenzo[b]thiophen-4-amine hydrochloride is stirred in methylene chloride-water and 5% sodium hydroxide solution is added gradually until the pH is about 10. The methylene chloride layer is removed and the aqueous layer is extracted with methylene chloride. The organic layers are combined, dried over magnesium sulfate, and evaporated to dryness to afford the oily amine. The amine is stirred in 500 ml. of ethyl acetate under nitrogen atmosphere and 25.4 grams of triethylamine is added. After about 15 minutes, 20.9 grams of carbon disulfide is added to afford a copius precipitate. An additional 200 ml. of ethyl acetate is added and the solid is pulverized with a spatula. After an hour of stirring, 51.5 grams of dicyclohexyl carbodiimide is added and stirring is continued for an overnight period. Subsequently, the mixture is heated at about 50° C. for 2 hours and cooled. The solid is removed by filtration and washed with ethyl acetate. The filtrate is evaporated to afford a mixture of solid and mostly oil. The solid is removed by filtration after either is added. The ether filtrate is evaporated to dryness to afford the crude isothiocyanate, which is purified by chromatography on a dry-column of silica gel using 65/35 (volume/volume) of petroleum ether/methylene chloride.

EXAMPLE 34

Preparation of N-(4,5,6,7-tetrahydrobenzo[b]thien-4-yl)-4-piperidinethiocarboxamide In 50 ml. of tetrahydrofuran, 5.85 grams of 4,5,6,7-tetrahydrobenzo[b]thien-4-yl isothiocyanate is stirred and 2.81 grams of piperidine is added. An exotherm is observed and the temperature rises to about 40° C. to 50° C. After 2.5 hours, the mixture is heated at reflux temperature for 3.5 hours. After stirring overnight, the mixture is evaporated to dryness to afford a sticky yellow-brown solid. Ether is added to this material and the off-white, insoluble product is collected. The crude product, 5.25 grams, melts at 102° C. to 104° C.

EXAMPLE 35

The following compounds set forth in Table IX below were prepared by using the methods described in Example 3 and Example 5 and using the corresponding amines (diethyl ether solvent) or amine hydrochlorides (tetrahydrofuran solvent) with the appropriate isocyanates or isothiocyanates.

TABLE IX

| $R_5$ | $R_6$ | $R_1$ | X | $R_3$ | $R_2$ | Reaction Solvent | Melting Point in degrees C. |
|---|---|---|---|---|---|---|---|
| H | H | —CH$_3$ | O | H | n-hexyl | ether* | 70.5–74.5 |
| H | H | —CH$_3$ | S | H | ethyl | ether | 104–107 |
| —CH$_3$ | H | H | S | H | ethyl | THF** | 118–121 |
| —CH$_3$ | H | H | O | H | ethyl | THF | 209–211 |
| —CH$_3$ | H | H | O | H | sec-butyl | THF | 182.5–185 |
| —CH$_3$ | H | H | O | H | n-hexyl | THF | 118–120 |
| H | —CH$_3$ | H | S | H | ethyl | THF | 120.5–123.5 |
| H | —CH$_3$ | H | O | H | sec-butyl | THF | 197–198 |
| H | —CH$_3$ | H | O | H | n-hexyl | THF | 148–150 |

TABLE IX-continued

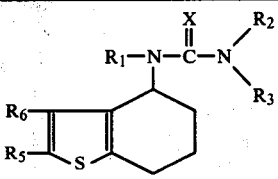

| R5 | R6 | R1 | X | R3 | R2 | Reaction Solvent | Melting Point in degrees C. |
|----|----|----|---|----|----|------------------|-----------------------------|
| H | H | H | O | H | —CH$_2$CH=CH$_2$ | THF | 175–176 |
| H | H | H | O | H | —CH$_2$CO$_2$C$_2$H$_5$ | THF | 147–149 |
| H | H | H | S | H | —C(=O)—C$_6$H$_5$ | ether | 122–125 |
| H | H | H | O | H | —CH$_2$-(3,4-methylenedioxyphenyl) | ether | 219–221 |
| H | H | H | O | H | -n-C$_{12}$H$_{25}$ | ether | 109–111 |
| H | H | H | S | H | cyclopentyl | ether | 122–125 |
| H | H | H | O | H | (4,5,6,7-tetrahydrobenzothiophen-4-yl) | ether | 279–283 |
| H | H | H | O |   | —(CH$_2$)$_4$— | ether | 137–139 |
| H | H | H | O |   | —(CH$_2$)$_5$— | ether | 128–130 |
| H | H | H | O | -n-C$_4$H$_9$ | -n-C$_4$H$_9$ | ether | 94–96 |
| H | H | H | S | H | —CH$_2$—CH$_2$-(2-pyridyl) | THF | oil |
| H | H | H | O | H | —CH$_2$CH$_2$—OH | ether | 140–154 |
| H | H | H | S |   | —(CH$_2$)$_5$— | THF | 103–106 |
| H | H | H | S | H | -n-C$_8$H$_{17}$ | THF | 66–69 |
| H | H | H | S | H | cyclopropyl | THF | 125–129 |
| H | H | H | S | H | —CH$_2$CH=CH$_2$ | THF | 101–103 |
| H | H | H | S | H | —CH$_2$-(2,3-methylenedioxyphenyl) | THF | 123–127 |
| H | H | H | S | H | —CH$_2$-(4-chlorophenyl) | THF | 137–144 |
| H | H | H | O | H | —CH$_2$—C≡CH | ether | 188–189 |
| H | H | H | O | H | (1,2,3,4-tetrahydronaphthalen-1-yl) | THF | 287–292 |
| H | H | H | O |   | 1,3-dithiolan-2-ylidene | ether | 126–128 |
| H | H | H | O | H | 1,3-thiazolin-2-yl | THF | 175–179 |

TABLE IX-continued

Structure: $R_1-N-\underset{\underset{||}{X}}{C}-N\underset{R_3}{\overset{R_2}{<}}$ attached to a tetrahydrobenzothiophene with $R_5, R_6$ on the thiophene ring.

| $R_5$ | $R_6$ | $R_1$ | X | $R_3$ | $R_2$ | Reaction Solvent | Melting Point in degrees C. |
|---|---|---|---|---|---|---|---|
| H | H | H | O | H | -C₆H₄-OCH₃ (p-methoxyphenyl) | CH₂CL₂ | 223–226 |
| H | H | H | O | —CH₂—CH=CH₂ | —CH₂CH=CH₂ | ether | 69–72 |
| H | H | H | S | —CH₃ | —OCH₃ | CH₂CL₂ | 74–77 |
| H | H | H | O | H | —OC₂H₅ | CH₂Cl₂ | 90–94 |
| H | H | H | O | H | —OCH₂—CH=CH₂ | CH₂Cl₂ | 70–73 |
| H | H | H | O | cyclohexyl | —OH | CH₂Cl₂ | 180–181 |
| H | H | H | O | H | —O-n-C₆H₁₃ | ether | 54–57 |
| H | H | H | O | —CH(CH₃)₂ | —OH | CH₂Cl₂ | 113–116 |
| H | H | H | O | —CH₂—CH=CH₂ | —CH₂—CH=CH₂ | ether | 69–72 |
| —CH₃ | H | H | O | H | H | H₂O | 234.5–236.5 |
| —CH₃ | H | H | O | H | -n-C₆H₁₃ | THF | 111–121 |
| H | —CH₃ | H | O | H | H | H₂O | 225–227 |
| —CH₃ | —CH₃ | H | S | H | —C₂H₅ | THF | 153–157 |
| —CH₃ | —CH₃ | H | O | H | -2-C₄H₉ | THF | 181–183.5 |
| —CH₃ | —CH₃ | H | O | H | -C₆H₄-Cl (p-chlorophenyl) | THF | 203–209 |
| —CH₃ | —CH₃ | H | O | H | H | H₂O | 233–237 |
| H | H | H | O | H | —CN | H₂O | 142–145 |
| H | H | H | O | —(CH₂)₂—N(CO₂C₂H₅)—(CH₂)₂— | | ether | 110–113 |
| H | H | H | O | H | -C₆H₃(CH₃)(Br) (3-bromo-4-methylphenyl) | ether | 235–236 |
| H | H | H | O | H | 2-adamantyl | ether | 225–227 |
| H | H | H | O | H | indanyl | ether | 280–282 |
| H | H | H | O | H | -n-C₄H₉ | CH₂Cl₂ | 159–161 |
| H | H | H | O | H | —CH₂CN | THF | 179–181 |
| H | H | H | O | H | —CH₂—CH₂—OCH₃ | ether | 142–144 |
| H | H | H | O | —(CH₂)₂—C(=O)—(CH₂)₂— | | ether | 139–140 |
| H | H | H | O | H | —CH₂CH₂—S—CH₃ | ether | 128–130 |
| H | H | H | O | —(CH₂)₂—C(spiro to hydantoin with N—C₆H₅)—(CH₂)₂— | | ether | 235–238 |
| H | H | H | O | H | —CH₂-(2-furyl) | ether | 183–185 |
| H | H | H | O | —CH₃ | —CH₂—C≡CH | ether | 105–108 |
| H | H | H | O | H | —CH₂—C(CH₃)=CH₂ | ether | 182–185 |
| H | H | H | O | H | —NH—CO₂CH₃ | ether | 183–186 |

TABLE IX-continued

Structure:
$R_1-N(-)-C(=X)-N(R_2)(R_3)$ attached at the 4-position of a 4,5,6,7-tetrahydrobenzo[b]thiophene bearing $R_5$, $R_6$ on the thiophene ring.

| $R_5$ | $R_6$ | $R_1$ | X | $R_3$ | $R_2$ | Reaction Solvent | Melting Point in degrees C. |
|---|---|---|---|---|---|---|---|
| H | H | H | O | H | $-CH_2-N(H)-CO-NH-$(4,5,6,7-tetrahydrobenzo[b]thien-4-yl) | CH$_3$OH | 278–279 |
| H | H | H | O | H | $-CH_2-$(3-pyridyl) | CH$_2$Cl$_2$ | 171–172 |
| H | H | H | O | H | $-CH_2-$(1-methyl-3-pyridinium iodide) | CH$_3$OH | 184–187 |
| H | H | H | O | H | $-$(4-chlorophenyl) | CH$_2$Cl$_2$ | 234–237 |
| H | H | H | O | H | $-CH_2-$(2-thienyl) | ether | 195–197 |
| H | H | H | O | $-CH_2-C\equiv CH$ | $-CH_2-C\equiv CH$ | ether | 118–120 |
| H | H | H | O | H | $-CH_2-$(4-pyridyl) | CH$_2$Cl$_2$ | 201–204 |
| H | H | H | O | H | $-CH_2-$(2-pyridyl) | CH$_2$Cl$_2$ | 192–195 |
| H | H | H | O | H | $-CH_2-$(4-methoxyphenyl) | CH$_2$Cl$_2$ | 188–191 |
| H | H | H | O | H | $-NH-CO-$(2-furyl) | CH$_2$Cl$_2$ | 201–203 |
| H | H | H | O | H | $-N$(piperazinyl)$N-C_6H_5$ | CH$_2$Cl$_2$ | 141–144 |
| H | H | H | O | H | $-CH_2CF_3$ | CH$_2$Cl$_2$ | 208–211 |
| H | H | H | O | $-CH_3$ | $-CH_2C_6H_5$ | CH$_2$Cl$_2$ | 68–70 |
| H | H | H | O | H | -t-butyl | CH$_2$Cl$_2$ | 187–192 |
| H | H | H | O | H | $-CH_2-$(4-chlorophenyl) | CH$_2$Cl$_2$ | 216–217 |
| H | H | H | O | H | $-CH_2CH_2-N(CH_3)_2$ | CH$_2$Cl$_2$ | 146–149 |
| H | H | H | O | H | $-CH_2CH(OCH_3)_2$ | CH$_2$Cl$_2$ | 125–128 |
| H | H | H | O | H | cyclopropyl | CH$_2$Cl$_2$ | 175–178 |
| H | H | H | O | H | (1,3-thiazol-2-yl) | THF | 207–210 |
| H | H | H | O | $-CH_2C_6H_5$ | $-CH_2C\equiv CH$ | CH$_2$Cl$_2$ | 112–115 |

TABLE IX-continued

Structure: $R_1$-N-C(=X)-N($R_2$)($R_3$) attached at the 4-position of 4,5,6,7-tetrahydrobenzo[b]thiophene; $R_5$, $R_6$ on thiophene positions 2,3.

| $R_5$ | $R_6$ | $R_1$ | X | $R_3$ | $R_2$ | Reaction Solvent | Melting Point in degrees C. |
|---|---|---|---|---|---|---|---|
| H | H | H | O | | —(CH$_2$)$_2$—N(4-methoxyphenyl)—(CH$_2$)$_2$— (cyclic) | CH$_2$Cl$_2$ | 129–133 |
| H | H | H | O | H | 4-NO$_2$-C$_6$H$_4$— | CH$_2$Cl$_2$ | 231–234 |
| H | H | H | O | H | 3,5-(CH$_3$)$_2$-C$_6$H$_3$— | CH$_2$Cl$_2$ | 241–242.5 |
| H | H | H | O | H | 2,4-Cl$_2$-C$_6$H$_3$— | CH$_2$Cl$_2$ | 242–245 |
| H | H | H | O | H | 3,4-(OCH$_3$)$_2$-C$_6$H$_3$— | CH$_2$Cl$_2$ | 200–204 |
| H | H | H | O | H | 4-OC$_2$H$_5$-C$_6$H$_4$— | CH$_2$Cl$_2$ | 221–225 |
| H | H | H | O | H | 4-OC$_4$H$_9$-C$_6$H$_4$— | CH$_2$Cl$_2$ | 183–186 |
| H | H | H | O | —CH$_2$C$_6$H$_5$ | —OH | CH$_2$Cl$_2$ | 121–123 |
| H | H | H | O | | —CH$_2$-(1,2-C$_6$H$_4$)-(CH$_2$)$_2$— (cyclic) | CH$_2$Cl$_2$ | 143–146 |
| H | H | H | O | H | —O—C$_6$H$_5$ | CH$_2$Cl$_2$ | 159–161 |
| H | H | H | O | —C$_6$H$_5$ | —OH | CH$_2$Cl$_2$ | 131–133 |
| H | H | H | O | H | —C(=O)—CH$_3$ | THF | 173–176 |
| H | H | H | S | H | —CO$_2$C$_2$H$_5$ | THF | 146–148 |

TABLE IX-continued $$R_1-N-\underset{\underset{\|}{C}}{X}-N\underset{R_3}{R_2}$$

(attached to 4,5,6,7-tetrahydrobenzo[b]thiophene with $R_5$, $R_6$ substituents)

| $R_5$ | $R_6$ | $R_1$ | X | $R_3$ | $R_2$ | Reaction Solvent | Melting Point in degrees C. |
|---|---|---|---|---|---|---|---|
| H | H | H | O | H | 2,4-dimethoxyphenyl ($OCH_3$, $OCH_3$) | $CH_2Cl_2$ | 206–207 |
| H | H | H | O | H | 3-methoxyphenyl ($OCH_3$) | $CH_2Cl_2$ | 176–179 |
| H | H | H | O | H | $-N(CH_3)_2$ | ether | 125–128 |
| H | H | H | O | H | $-\overset{O}{\underset{\|}{C}}-CCl_3$ | THF | 149–151 |
| H | H | H | S | H | 4-methoxyphenyl ($OCH_3$) | THF | 149–150.5 |
| H | H | H | O | H | $-O-C_6H_5$ | ether | 159–161 |
| H | H | H | O | H | $-O-CH_2-CO_2H$ | $CH_2Cl_2$ | 142–145 |

*diethyl ether
**tetrahydrofuran

EXAMPLE 36

Preparation of 4,5,6,7-tetrahydro-2,3-dimethylbenzo[b]thiophen-4-amine hydrochloride 2,3-Dimethyl-6,7-dihydro-5H-benzo[b]thiophen-4-one is prepared in the manner described by Napier and Chu [International Journal of Sulfur Chemistry, A, 1, 62–64 (1971)]. This ketone is converted to 4-formylamino-4,5,6,7-tetrahydro-2,3-dimethylbenzo[b]thiophene by the method described by Kloetzel, Little, and Fish [Journal of Organic Chemistry, 18, 1511–1515 (1953)]. Hydrolysis of this formamido derivative is accomplished by using the method described in Example 19 to afford 4,5,6,7-tetrahydro-2,3-dimethylbenzo[b]thiophen-4-amine hydrochloride.

3-Methyl-6,7-dihydro-5H-benzo[b]thiophen-4-one is prepared similarly and converted to 3-methyl-4,5,6,7-tetrahydro benzo[b]thiophen-4-amine hydrochloride by the above sequence.

EXAMPLE 37

Preparation of 2-methyl-4,5,6,7-tetrahydrobenzo[b]thiophen-4-amine hydrochloride 2-Methylthiophene is converted to 2-methyl-6,7-dihydro-5H-benzo[b]thiophen-4-one by the method described by Fieser and Kennelly [Journal American Chemical Society, 57, 1611 (1935)]. This ketone is further converted to 2-methyl-4,5,6,7-tetrahydrobenzo[b]thiophen-4-amine hydrochloride by the methods cited in Example 36.

EXAMPLE 38

Preparation of 2-nitro-N-formyl-4,5,6,7-tetrahydrobenzo[b]thien-4-ylurea

Acetic anhydride (30.8 ml.) is cooled to −10° C. to −12° C. and to the stirred solution is added dropwise 70% nitric acid (4 g. or 44.5 mmol). Over a period of 0.5 hour, N-formyl-4,5,6,7-tetrahydrobenzo[b]thiophen-4-amine (7.24 grams or 40 mmol) is added and the mixture is allowed to warm to room temperature over 2.5 hours and poured onto ice-water mixture (200 ml.). After stirring overnight, the sticky solid is filtered off and washed well with water. The air-dried, dark, sticky solid is triturated with ether (~20 ml.), and the resulting nitro compound is filtered and washed with ether (10 ml.). The product, 2-nitro-N-formyl-4,5,6,7-tetrahydrobenzo[b]thiophen-4-amine, melts at 116° C. to 120° C. and weighs 3.25 grams.

Hydrolysis of the above formamide is accomplished by the method described in Example 19 to afford 2-nitro-4,5,6,7-tetrahydrobenzo[b]thiophen-4-amine hydrogen chloride, melting point >260° C.; infrared spectrum shows $NO_2$ bands at 1520 cm$^{-1}$ and 1335 cm$^{-1}$.

Conversion of the amine hydrogen chloride salt to 2-nitro-4,5,6,7-tetrahydrobenzo[b]thien-4-ylurea is accomplished by the method described in Example 10. It melts at 211° C. with decomposition after recrystallization from MeOH.

EXAMPLE 39

Preparation of
1-methyl-3-(5-iodo-4-methyl-4,5,6,7-tetrahydrobenzo[b]thien-4-yl)urea By the method of Kloetzel, Little, and Fish [Journal of Organic Chemistry, 18, 1511 (1953)], 4,5,6,7-tetrahydro-4-methylbenzo[b]thiophen-4-ol is prepared and dehydrated with fused sodium hydrogen sulfate by heating to afford 6,7-dihydro-4-methylbenzo[b]thiophen, boiling point 75°/0.9 Torr. This olefin (3 grams) is stirred with 3.9 grams of silver isocyanate in 50 ml. of dry ether under $N_2$ atmosphere at −10° C. and 5.07 grams of iodine is added. After stirring for 1.25 hour at −10° C. to 0° C. and then at 10° C. to 15° C. for 1.5 hours, the mixture is filtered over diatomaceous earth and the filter cake is washed with ether thoroughly. The filtrate is then treated with 2 ml. of 40% aqueous methyl amine to afford 1.62 grams, melting point 122° C. to 123° C., of 1-methyl-3-(5-iodo-4-methyl-4,5,6,7-tetrahydrobenzo[b]thien-4-yl)urea.

EXAMPLE 40

Preparation of
1-methyl-3-(4-methyl-4,5,6,7-tetrahydrobenzo[b]thien-4-yl)urea

Deiodination of 1-methyl-3-(5-iodo-4-methyl-4,5,6,7-tetrahydrobenzo[b]thien-4-yl)urea is accomplished by treating a methanol mixture of this compound with palladium on carbon and magnesium oxide in a Paar hydrogenator at 50 psig. After uptake of the hydrogen is completed, the mixture is filtered through diatomaceous earth and filtrate is evaporated to dryness to afford 1-methyl-3-(4-methyl-4,5,6,7-tetrahydrobenzo[b]thien-4-yl)urea, melting point 135° C. to 145° C.

EXAMPLE 41

Preparation of
7,7-dimethyl-4,5,6,7-tetrahydrobenzo[b]thien-4-ylurea

By the method described in Example 36 (first reference), 7,7-dimethyl-4,5,6,7-tetrahydrobenzo[b]thiophen-4-one is prepared and converted to 7,7-dimethyl-4,5,6,7-tetrahydrobenzo[b]thiophen-4-amine hydrochloride, melting point 211.5° C. to 215° C., by the remaining methods described in Example 36. The amine hydrochloride is converted to 7,7-dimethyl-4,5,6,7-tetrahydrobenzo[b]thien-4-ylurea, melting point 184° C. to 189° C. dec., by the method described in Example 10.

EXAMPLE 42

Preparation of
6,6-dimethyl-4,5,6,7-tetrahydrobenzo[b]thien-4-ylurea

By the method described in Example 36 (first reference), 6,6-dimethyl-4,5,6,7-tetrahydrobenzo[b]thiophen-4-one is prepared and converted to 6,6-dimethyl-4,5,6,7-tetrahydrobenzo[b]thiophen-4-amine hydrochloride (melting point >300° C.) by the two remaining methods cited in Example 36. The amine hydrochloride is then converted to 6,6-dimethyl-4,5,6,7-tetrahydrobenzo[b]thien-4-ylurea, melting point 174° C. to 178° C., by the method outlined in Example 10.

EXAMPLE 43

Preparation of
1-methyl-3-(5-methyl-4,5,6,7-tetrahydrobenzo[b]thien-4-yl)urea

Diisopropylamine (7.3 grams or 72 mmol) is cooled and stirred in 60 ml. of dry tetrahydrofuran (THF) and 45 ml. (72 mmol) of 1.6 N n-butyl lithium in hexane is added to <−5° C. Five minutes later a solution of 4,5,6,7-tetrahydrobenzo[b]thiophen-4-one, 12 grams of 60 mmol in 30 ml. of THF is added dropwise at 0° C. to −10° C. After stirring for 30 minutes at room temperature, 38 grams (270 mmol) of methyl iodide is added at <30° C. After stirring for 40 hours at room temperature, 100 ml. of water is added and the THF is removed in vacuo. The residue is extracted with 3×50 ml. of methylene chloride and the combined extracts are washed with 50 ml. of 2 N hydrochloric acid, 50 ml. of 1 M sodium carbonate, and 50 ml. of brine, respectively. The solution is dried (magnesium sulfate) and evaporated in vacuo to afford 9.46 grams of light brown oil. The oil is purified by chromatography on a silica-gel dry column using 1:1 hexane/methylene chloride to afford 6.9 grams of 5-methyl-4,5,6,7-tetrahydrobenzo[b]thiophen-4-one. This ketone is converted to 5-methyl-4,5,6,7-tetrahydrobenzo[b]thiophen-4-amine hydrochloride by the method cited in Example 36 and then the amine hydrochloride is converted to 1-methyl-3-(5-methyl-4,5,6,7-tetrahydrobenzo[b]thien-4-yl)urea, melting point 173° C. to 182° C., by the method described in Example 1.

Similarly, alkylation of 4,5,6,7-tetrahydrobenzo[b]thiophen-4-one with ethyl iodide, propyl iodide, and butyl iodide affords the corresponding 5-alkyl ketones, which are converted in the above manner to 1-methyl-3-(5-ethyl-4,5,6,7-tetrahydrobenzo[b]thien-4-yl)urea, 1-methyl-3-(5-propyl-4,5,6,7-tetrahydrobenzo[b]thien-4-yl)urea, and 1-methyl-3-(5-butyl-4,5,6,7-tetrahydrobenzo[b]thien-4-yl)urea, respectively.

EXAMPLE 44

Preparation of
1-(methoxymethyl)-3-(4,5,6,7-tetrahydrobenzo[b]thien-4-yl)urea

In 150 ml. of methanol, 8.24 grams of 4,5,6,7-tetrahydrobenzo[b]thien-4-ylurea is stirred and 2.1 grams of sodium hydroxide pellets followed by 2.31 grams of paraformaldehyde in 50 ml. of methanol are added. The mixture is heated at reflux for 10 hours and cooled to afford crystals which are collected. The filtrate is evaporated to dryness and the residue is washed with water to afford 6.7 grams of solid. Recrystallization of the combined fractions from acetone-hexane gives 5.3 grams of 1-(methoxymethyl)-3-(4,5,6,7-tetrahydrobenzo[b]thien-4-yl)urea, melting point 160° C. to 162° C.

EXAMPLE 45

Preparation of 4,5,6,7-tetrahydrobenzo[b]thien-4-yl thiourea

A mixture of 13.21 grams of 1-benzoyl-3-(4,5,6,7-tetrahydrobenzo[b]thien-4-yl)thiourea in 100 ml. of 10% sodium hydroxide solution is heated to reflux for 10 minutes and cooled. The solid is collected and dissolved in 95% ethanol and the solution is evaporated to afford 9 grams of white solid. Recrystallization of this solid from chloroform/hexane affords 8.13 grams of 4,5,6,7- tetrahydrobenzo[b]thien-4-yl thiourea, melting point 129° C. to 131° C.

EXAMPLE 46

Preparation of 4,5,6,7-tetrahydro-7-oxobenzo[b]thien-4-ylurea

A sample of 6 grams of 4,5,6,7-tetrahydrobenzo[b]thien-4-ylurea is dissolved in 375 ml. of 50% aqueous acetic acid and 75 grams of ceric ammonium nitrate is added in portions over a 10 minute period with stirring at 25° C. to 35° C. The pale-orange solution is stirred for another 5 minutes and 100 ml. of water is added. The solution is extracted twice with ethyl acetate (450 ml. and 350 ml.) and the combined extracts are washed with 100 ml. of water. The organic extract is evaporated to dryness in vacuo and the brown residue is crystallized from methanol to afford 2.37 grams of 4,5,6,7-tetrahydro-7-oxobenzo[b]thien-4-ylurea, melting point 237° C. to 238° C. dec. Recrystallization from methanol affords purified product, melting point 245° C. to 246° C. dec.

Similarly, 1-methyl-3-(4,5,6,7-tetrahydro-7-oxobenzo[b]thien-4-yl)urea, 1-ethyl-3-(4,5,6,7-tetrahydro-7-oxobenzo[b]thien-4-yl)urea, 1-n-hexyl-3-(4,5,6,7-tetrahydro-7-oxobenzo[b]thien-4-yl)urea, 1-n-dodecyl-3-(4,5,6,7-tetrahydro-7-oxobenzo[b]thien-4-yl)urea, and 1-phenyl-3-(4,5,6,7-tetrahydro-7-oxobenzo[b]thien-4-ylurea, and the optical isomers of the 4,5,6,7-tetrahydro-7-oxobenzo[b]thien-4-ylureas are prepared by the above procedure starting with the corresponding ureas.

Substitution of the ceric ammonium nitrate with silver oxide, chromic anhydride or sodium dichromate also affords the above mentioned 7-oxo compounds. Chromic anhydride in acetic anhydride, followed by hydrolysis, also affords the 7-oxo compounds. The above-mentioned 7-oxo derivatives are also prepared by oxidizing their corresponding 7-hydroxycycloalkano[b]thien-4-ylurea in a similar manner.

EXAMPLE 47

Preparation of 1,1-dimethyl-3-(4,5,6,7-tetrahydro-7-oxobenzo[b]thien-4-yl)urea

A solution of 4,5,6,7-tetrahydro-7-oxobenzo[b]thiophen-4-amine (10.5 g.) in tetrahydrofuran (70 ml.) is added dropwise under nitrogen atmosphere to a solution of dimethylcarbamoyl chloride (6.72 g.) and triethylamine (12.6 g.) in tetrahydrofuran (70 ml.). After stirring for 20 hours, the mixture is evaporated to dryness and cold water (100 ml.) is added to the residue. The solid product is collected and air-dried. Recrystallization from acetone-hexane affords 3.7 g. of 1,1-dimethyl-3-(4,5,6,7-tetrahydro-7-oxobenzo[b]thien-4-yl)urea, m.p. 195° C. to 197° C.

Similarly, dibutylcarbamoyl chloride, dipropylcarbamoyl chloride and diethylcarbamoyl chloride are used in place of dimethylcarbamoyl chloride to afford 1,1-dibutyl-, 1,1-dipropyl-, and 1,1-diethyl-3-(4,5,6,7-tetrahydro-7-oxo-benzo[b]thien-4-yl)urea, respectively.

Substitution of the above-mentioned carbamoyl chlorides with the corresponding thiocarbamoyl chlorides affords the corresponding thioureas.

EXAMPLE 48

Preparation of 1,1-dimethyl-3-(4,5,6,7-tetrahydrobenzo[b]thien-4-yl)urea

Equimolar quantities of 4,5,6,7-tetrahydrobenzo[b]thiophen-4-amine, dimethylcarbamoyl chloride and sodium hydroxide in water are stirred overnight. The crude product, 1,1-dimethyl-3-(4,5,6,7-tetrahydrobenzo[b]thien-4-yl)urea is collected and washed well with water. Recrystallization from acetone-hexane-ether affords pure product, m.p. 117° C. to 120° C.

Similarly, diethyl-, dipropyl-, and dibutylcarbamoyl chloride are reacted with 4,5,6,7-tetrahydrobenzo[b]thiophen-4-amine to afford 1,1-diethyl-, 1,1-dipropyl-, and 1,1-dibutyl-3-(4,5,6,7-tetrahydrobenzo[b]thien-4-yl)urea, respectively. Substitution of the above-mentioned carbamoyl chlorides with the corresponding thiocarbamoyl chlorides affords the corresponding thioureas.

EXAMPLE 49

Preparation of (+)- and (−)-4,5,6,7-tetrahydrobenzo[b]thiophen-4-amine

A mixture of 145.15 grams of (−)-4,5,6,7-tetrahydrobenzo[b]thiophen-4-ammonium (R)-N-benzoyl glutamate in 900 ml. of water and 50 grams of ice is stirred with 82 grams of NaOH in 1265 ml. of water. The mixture is extracted with 700 ml. and 500 ml. volumes of diethyl ether and the combined ether solutions are washed with brine and dried over $Na_2SO_4$. The ether solution is evaporated in vacuo to afford 52.85 grams of a colorless liquid; $[\alpha]_D^{24} = +57.12°$ (c, 4.16 in benzene) for the (+)-amine.

Similarly, (+)-4,5,6,7-tetrahydrobenzo[b]thiophen-4-ammonium (S)-N-benzoyl glutamate was treated with base to afford the (−)-amine, $[\alpha]_D^{25} = -56.35°$ (c, 3.05 in benzene).

EXAMPLE 50

Preparation of (−)- and (+)-N-(4,5,6,7-tetrahydrobenzo[b]thien-4-yl)formamide

In nitrogen atmosphere, 48.9 grams of 97% formic acid is added dropwise (over 15 minutes) to a stirred mixture of (+)-4,5,6,7-tetrahydrobenzo[b]thiophen-4-amine in 275 ml. of toluene at below 35° C. The mixture is heated at reflux using a Dean-Stark trap to remove water by azeotropic distillation. After 5.5 hours, very little water is distilled and thus the mixture is cooled. On cooling, the white product which crystallizes is collected. Additional product is obtained when the toluene filtrate is concentrated. The combined crops are washed with 500 ml. of water and then with 150 ml of cold hexane. The yield of the (−)-formamide is 60.5 grams, m.p. 132.5°–134° C., $[\alpha]_D^{24} = -119.67°$ (c, 4.18 in $CHCl_3$), $[\alpha]_D^{24} = -126.4°$ (c, 4.01 in HOAc).

Similarly, the (−)-4,5,6,7-tetrahydrobenzo[b]thiophen-4-amine is converted to (+)-N-(4,5,6,7-tetrahydrobenzo[b]thien-4-yl)formamide, m.p. 132°–135° C., $[\alpha]_D^{25} = +126.99°$ (c, 4.08 in HOAc).

EXAMPLE 51

Preparation of
(−)-N-(4,5,6,7-tetrahydro-7-oxobenzo[b]thien-4-yl)formamide

Ceric ammonium nitrate (726.9 grams) is added portionwise to a stirred solution of 59.6 grams of (−)-N-(4,5,6,7-tetrahydrobenzo[b]thien-4-yl)formamide in 1712 ml. of 50% aqueous acetic acid. The addition is completed in half an hour and the temperature is kept at 25°–28° C. After 15 minutes of stirring, the mixture is saturated with NaCl and extracted with $CH_2Cl_2$ (2×1200 ml., 600 ml.) and the combined extracts are washed with 600 ml. of brine and then with 250 ml. of water. The water is counter-extracted with 250 ml. of $CH_2Cl_2$ and the $CH_2Cl_2$ solution is added to the main $CH_2Cl_2$ solution. The $CH_2Cl_2$ solution is evaporated to dryness in vacuo and the residual dark, gummy residue is stirred with 500 ml. of dry diethyl ether for 1.5 hour and the large lumps of solid are pulverized. The title compound is then collected, washed with diethyl ether, and dried. This gives 48.65 g., m.p. 130°–136° C., $[\alpha]_D^{24} = 144.4°$ (c, 0.51 in HOAc).

EXAMPLE 52

Preparation of
(+)-N-(4,5,6,7-tetrahydro-7-oxobenzo[b]thien-4-yl)formamide

The title compound is prepared in the same manner as the (−) enantiomer (Example 51) and the product melts at 129°–134° C.; $[\alpha]_D^{25.5} = +140.3°$ (c, 1.06 in HOAc).

EXAMPLE 53

Preparation of
(+)-4,5,6,7-tetrahydro-7-oxobenzo[b]thiophen-4-amine hydrochloride A mixture of (+)-N-(4,5,6,7-tetrahydro-7-oxobenzo[b]thien-4-yl)formamide (52.65 grams) in 525 ml. of 95% ethanol and 525 ml. of 2 N HCl is heated at reflux for two hours. The mixture is cooled, filtered through glass wool and the filtrate is evaporated to dryness. The dark solid is dissolved in 180 ml. of water and the insoluble material is collected by filtration. The filter cake is washed with 70 ml. of water and the combined solution containing the title compound is used in the next operation. A 3 ml. solution is evaporated to dryness and the residue is dissolved in 95% ethanol. The ethanol solution is decolorized with activated carbon and filtered. The filtrate is evaporated to dryness to afford 0.5 grams of the title compound, m.p. 212°–214° C. (dec.), $[\alpha]_D^{26} = +13.56°$ (c, 0.59 in methanol).

Similarly, the (−)-4,5,6,7-tetrahydro-7-oxobenzo[b]thiophen-4-amine hydrochloride is prepared and used directly in the next operation as a solution.

EXAMPLE 54

Preparation of
(−)-4,5,6,7-tetrahydro-7-oxobenzo[b]thien-4-ylurea

The aqueous solution (280 ml.) of (+)-4,5,6,7-tetrahydro-7-oxobenzo[b]thiophen-4-amine hydrochloride from Example 53 is stirred while 40 grams of KOCN in 95 ml. of water is added dropwise. The mixture is warmed to 70° C. for 1.5 hour and cooled to 10° C. The light brown solid is collected and washed well with 700 ml. of water. The product is then stirred with 110 ml. of cold methanol, collected, and washed with 50 ml. of cold methanol to afford 48 grams of the title compound, m.p. 247°–249.5° C. (dec.), $[\alpha]_D^{24} = -97.16°$ (c, 0.14 in methanol).

EXAMPLE 55

Preparation of
(+)-4,5,6,7-tetrahydro-7-oxobenzo[b]thien-4-ylurea

As described in the preparation of the (−) enantiomer, the title compound is prepared in 82% yield; m.p. 243°–246° C. (dec.); $[\alpha]_D^{25.5} = +84.66°$ (c, 0.19 in methanol).

EXAMPLE 56

Preparation of
(−)-4,5,6,7-tetrahydro-7-hydroxybenzo[b]thien-4-ylurea, isomers A and B In 2.5 liters of ethanol, 34.85 grams of (−)-4,5,6,7-tetrahydro-7-oxobenzo[b]thien-4-ylurea is stirred and 9.8 grams of $NaBH_4$ is added. The mixture is stirred overnight at room temperature, 1400 ml. of water is added, and after stirring for 0.5 hour the ethanol is evaporated in vacuo. The mixture is cooled and 25–30 ml. of acetic acid is added until no more foaming occurs. The mixture is stirred for 0.75 hour, filtered to collect the first crop and this solid is washed with water and air dried. This solid is recrystallized from acetone and then from acetone/methanol to give 6.75 g. of isomer B of the title compound, m.p. 211°–213° C. (dec.), $[\alpha]_D^{25.5} = -23.23°$ (c, 3.11 in methanol). This material contains 92% isomer B and 8% isomer A when assayed by high pressure liquid chromatography.

The original mother liquor is evaporated in vacuo, using ethanol to aid in removing water as an azeotrope. The residue is extracted twice with boiling acetone (1400 ml. portions) and the extracts are concentrated until crystals formed. A total of 13.1 g. which contains both isomers A and B is obtained. By preparative high pressure liquid chromatography on silica gel using a solvent mixture (volume/volume) of 1800 hexane/1000 $CHCl_3$/425 methanol at a flowrate of 40 ml./minute, 180 milligrams of 86% pure isomer A of the title compound is separated. This material melts at 162°–167° C. (dec.); $[\alpha]_D^{25.5} = -93.56°$ (c, 2.02 in methanol).

The terms isomer A and isomer B are used for the geometric isomers of the title compound as the assignment of the cis and trans configurations have not been determined unequivocally.

EXAMPLE 57

Preparation of
(+)-4,5,6,7-tetrahydro-7-hydroxybenzo[b]thien-4-ylurea, isomers A and B In the same manner as described in reducing the (−)-4,5,6,7-tetrahydro-7-oxobenzo[b]thien-4-ylurea, (+)-4,5,6,7-tetrahydro-7-oxobenzo[b]thien-4-ylurea is reduced with $NaBH_4$ to afford isomer B of the title compound, m.p. 216°–217° C. (dec.), $[\alpha]_D^{25.5} = +18.51°$ (c, 2.11 in methanol). This isomer is 95% pure by high pressure liquid chromatography. Isomer A of the title compound is also purified by high pressure liquid chromatography as a 90–95% pure material, m.p. 160°–164° C. (dec.), $[\alpha]_D^{24.5} = -91.03°$ (c, 2.2 in methanol). The cis and trans configurations for isomers A and B have not been determined unequivocally.

EXAMPLE 58

Preparation of (−)-4,5,6,7-tetrahydrobenzo[b]thiophen-4-amine hydrochloride

A sample of 1.02 grams of (dl)-4,5,6,7-tetrahydro-7-oxobenzo[b]-thiophen-4-amine hydrochloride is treated with 0.8 grams of sodium hydroxide in 13 ml. of water and the free amine is extracted with chloroform several times (total volume 200 ml.). The chloroform extract is washed with brine, dried over Na$_2$SO$_4$ under nitrogen atmosphere, and the solution is evaporated to dryness to afford the liquid amine. The amine is dissolved in 5 ml. of methanol and a solution of 0.75 grams of (+)-tartaric acid in 10 ml. of methanol is added. The mixture is warmed slightly and allowed to cool to room temperature. The crystals are collected and fractionally crystallized from 85–90 ml. of 95% ethanol to afford 0.6 grams of salt. This salt is treated with 0.8 grams of NaOH in 13 ml. of water and the mixture is extracted several times with CHCl$_3$ (total volume 200 ml.) The combined extracts are washed with brine, dried over Na$_2$SO$_4$ under nitrogen and the solution is evaporated to dryness. The residual amine is dissolved in 10 ml. of acetone and treated with a saturated solution of HCl in isopropyl alcohol (1–2 ml.) until solid no longer forms. The solid title compound is collected and dried; melting point 219°–221° C. (dec.); $[\alpha]_D^{28} = 14.32°$ (c, 0.91 in methanol).

EXAMPLE 59

Preparation of and separation of 7-hydroxy-4,5,6,7-tetrahydrobenzo[b]thien-4-ylurea into the cis and trans isomers 7-Keto-4,5,6,7-tetrahydrobenzo[b]-thien-4-ylurea (0.5 grams, 2.38 mm) is suspended in ethanol (50 ml.) and to the stirred solution is added solid sodium borohydride (0.5 grams, 13.2 mm). After stirring overnight the mixture is treated cautiously with 5% aqueous acetic acid (20 ml.). After stirring 15 minutes the solvent is removed, the residue dissolved in a small volume of methanol and percolated through a 1½″ × 1¾″ silica gel dry column eluting with 20% methanolic methylene chloride. The resulting gum is crystallized from ethyl acetate/methanol to afford 66 mg. (13% Y) of the more polar (L.L.C) alcohol (B), melting point 194° C. to 197° C. The mother liquor material is separated into its two major components 7-hydroxy-4,5,6,7-tetrahydrobenzo[b]thien-4-ylurea by high pressure liquid chromatography on "Spherosil XOA 400" using the solvent system: hexane (1800 ml.)/methanol (425)/chloroform (1000) (flow rate ~ 13 ml./min.). This procedure affords the less polar alcohol A (29 mgs. 6% yield) melting point, 162° C. to 169° C. (methanol/ethyl acetate), and the more polar alcohol B (50 mg., 10% yield), melting point 197° C. to 198° C.

The following compounds set forth in Table X below were prepared by reducing an appropriately substituted 7-keto-4,5,6,7-tetrahydrobenzo[b]thien-4-ylurea with sodium borohydride in ethanol as described immediately hereinabove. Unless otherwise indicated in Table X, the products were isolated as a mixture of the cis and trans isomers.

TABLE X

[structure: 4,5,6,7-tetrahydrobenzo[b]thiophene with NH—C(=O)—N(R$_2$)(R$_3$) at position 4 and OH at position 7]

| R$_3$ | R$_2$ | Melting point in degrees C. |
|---|---|---|
| H | -n-C$_8$H$_{17}$ | 106–129 |
| H | —CH$_2$—CH=CH$_2$ | 173–176 |
| H | -iso-C$_3$H$_7$ | 180–187 |
| —CH$_3$ | —CH$_3$ | 218–225 |
| H | —CH$_3$ | 136–145 |
| H | —CH$_2$—C≡CH | 176–179 |
| —CH$_3$ | —OCH$_3$ | 179–182 |
| H | —C$_2$H$_5$ | 183–188 |
| H | —OCH$_3$ | 158–162 |
| H | H | 190–195 |

(mixture of dextrorotatory diastereomers; 62% isomer B)

EXAMPLE 60

Preparation of 2,4-bis[3′-methylureido]-4,5,6,7-tetrahydrobenzo[b]thiophene

2-Nitro-4-amino-4,5,6,7-tetrahydrobenzo[b]thiophene hydrochloride (0.5 grams, 2.13 mmol) is dissolved in concentrated hydrochloric acid (4.3 ml.). The stirred solution is treated with stannous chloride dihydrate (2.56 grams, 11.35 mmol) added in portions over a 10 minute period (solution becomes hot). The brown solution is stirred for 3 hours, added to ice/water (20 ml.), made alkaline with 10% sodium hydroxide and the turbid solution extracted 3 times with methylene chloride (total volume ca. 100 ml.). The combined methylene chloride extracts are washed once with brine (20 ml.), dried (sodium sulfate) and evaporated to afford a gum. The gum is dissolved in methylene chloride (10 ml.) and ether (10 ml.) and the stirred solution treated with a solution of methyl isocyanate (0.5 grams, 8.8 mmol) in ether (10 ml.), added over a 10-minute period. The mixture is stirred overnight, then evaporated to dryness and the residue recrystallized from hot methanol to afford 230 mg. (38% yield) of 2,4-bis[3′-methylureido]-4,5,6,7-tetrahydrobenzo[b]thiophene, melting point 233° C. to 234° C.

EXAMPLE 61

Preparation of N-formyl-4,5,6,7-tetrahydro-7-oxobenzo[b]thiophen-4-amine

In the manner described in Example 46, N-formyl-4,5,6,7-tetrahydrobenzo[b]thiophen-4-amine is oxidized with ceric ammonium nitrate to afford N-formyl-4,5,6,7-tetrahydro-7-oxobenzo[b]thiophen-4-amine, melting point 118° C. to 120° C. dec. This product is extracted from the reaction mixture with methylene chloride. The use of chromic anhydride in acetic anhydride followed by hydrolysis also affords the identical product.

Using the same work-up procedure, the following oxidants also afford the title compound which is isolated and/or analyzed for by spectroscopy (infrared and/or nuclear magnetic resonance). In Table XI below, the oxidant is expressed in terms of moles per mole of substrate.

TABLE XI

| Oxidant | Conditions | Yield |
|---|---|---|
| $K_2S_2O_8$ (2M)/$AgNO_3$ (catalytic) | In aqueous acetic acid at 50°C. | 27% |
| $KMnO_4$ (3.45M)/ $Ce(NH_4)_2(NO_3)_6$ (catalytic) | In aqueous acetic acid at less than 35°C. | 8% |
| tert-butyl chromate (4.1M) | In $CCl_4$ at room temp. for four hours | 33% |
| $CrO_3 \cdot 2$ pyridine (11.9M) | In $CH_2Cl_2$ at room temp. overnight | 40% |
| $Ce(SO_4)_2 \cdot 2H_2SO_4$ (4M) | In aqueous acetic acid at room temp. | 60% |
| $H_2O_2/V_2O_5$ (catalytic) (acetamide substrate instead of formamide) | In acetone at 34°C. overnight | 16% |
| $CrO_2Cl_2$ (2M) (acetamide substrate instead of formamide) | In $CH_2Cl_2$ at less than 10° C. | 8.5% |

EXAMPLE 62

Preparation of 4,5,6,7-tetrahydro-7-oxobenzo[b]thiophen-4-amine hydrochloride

In the manner described in Example 36, N-formyl-4,5,6,7-tetrahydro-7-oxobenzo[b]thiophen-4-amine is hydrolyzed with 2 N hydrochloric acid/ethanol to afford 4,5,6,7-tetrahydro-7-oxobenzo[b]thiophen-4-amine hydrochloride, melting point 230° C. to 232° C. (dec.).

The free amine is obtained by neutralizing the amine hydrochloride in water with sodium hydroxide solution. It is separated by extraction with $CHCl_3$ and removal of the $CHCl_3$ in vacuo affords 4,5,6,7-tetrahydro-7-oxobenzo[b]thiophen-4-amine.

EXAMPLE 63

Preparation of 4,5,6,7-tetrahydro-7-oxobenzo[b]thien-4-yl isocyanate and urea

Conversion of 4,5,6,7-tetrahydro-7-oxobenzo[b]thiophen-4-amine hydrochloride to 4,5,6,7-tetrahydro-7-oxobenzo[b]thien-4-yl isocyanate is accomplished by heating a toluene mixture of the hydrochloride at reflux temperature while phosgene is introduced. After the mixture becomes less cloudy, it is cooled and filtered. Evaporation of the filtrate affords the crude 4,5,6,7-tetrahydro-7-oxobenzo[b]thien-4-yl isocyanate; IR maximum = 2250 cm$^{-1}$.

Addition of $NH_3/CH_3OH$ solution to this isocyanate affords 4,5,6,7-tetrahydro-7-oxobenzo[b]thien-4-ylurea.

EXAMPLE 64

The following compounds set forth in Table XII below are prepared by allowing 4,5,6,7-tetrahydro-7-oxobenzo[b]thiophen-4-amine hydrochloride to react with RNCX in the presence of an equimolar quantity of triethylamine in solvents such as aromatic solvents, chlorinated hydrocarbons, ethers, lower alkyl $C_1$–$C_4$ ketones, or mixtures thereof.

TABLE XII

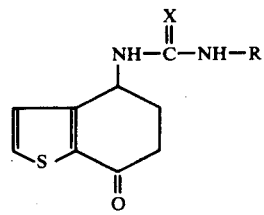

| | Product | | |
|---|---|---|---|
| RNCX | R | X | Melting Point in degrees C. |
| $CH_3NCO$ | $CH_3-$ | O | 212–215 |
| $C_2H_5NCO$ | $C_2H_5-$ | O | 188–190 |
| $CCl_3C(O)-NCO$ | $Cl_3C-C(O)-$ | O | 185–188 |
| $C_6H_5CH_2NCO$ | $C_6H_5CH_2-$ | O | |
| $C_2H_5NCS$ | $C_2H_5-$ | S | |
| $CH_3O-CH_2NCO$ | $CH_3-O-CH_2-$ | O | |
| $CH_3O-CH_2NCS$ | $CH_3-O-CH_2-$ | S | |
| $CH_3O-C_6H_4-NCO$ | $CH_3-C_6H_4-$ | O | |
| $CH_3NCS$ | $CH_3-$ | S | 161–164 |

EXAMPLE 65

The following compounds set forth in Table XIII below are prepared by reacting 4,5,6,7-tetrahydro-7-oxobenzo[b]thien-4-yl isocyanate with the appropriate amines in inert solvents, as described before in Example 35.

TABLE XIII

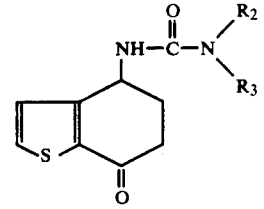

| | Product | |
|---|---|---|
| Amines | $R_3$ | $R_2$ |
| $NH_2-OCH_3$ | H | $-OCH_3$ |
| $NH_2-OH$ | H | $-OH$ |
| $CH_3NH-OH$ | $-CH_3$ | $-OH$ |
| $CH_3NH-OCH_3$ | $-CH_3$ | $-OCH_3$ |
| $CH_2=CH-CH_2-NH_2$ | H | $-CH_2-CH=CH_2$ |
| $CH\equiv C-CH_2-NH_2$ | H | $-CH_2-C\equiv CH$ |
| $(CH_3)_2NH$ | $-CH_3$ | $-CH_3$ |
| $C_6H_5CH_2NH_2$ | H | $-CH_2-C_6H_5$ |
| $C_2H_5NH_2$ | H | $-C_2H_5$ |
| n-$C_4H_9NH_2$ | H | -n-$C_4H_9$ |
| $CH_3C(O)-NH_2$ | H | $-C(O)-CH_3$ |
| 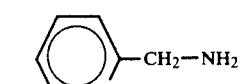 | H | 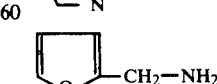 |
| 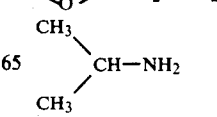 | H | —CH(CH_3)_2 |

EXAMPLE 66

By the method described in Example 59, the following compounds are prepared as cis and trans mixtures from their corresponding keto precursors:

Optically active isomers of 7-hydroxy-4,5,6,7-tetrahydrobenzo[b]thien-4-ylurea, 1-methyl-3-(7-hydroxy-4,5,6,7-tetrahydrobenzo[b]thien-4-yl)urea, 1-ethyl-3-(7-hydroxy-4,5,6,7-tetrahydrobenzo[b]thien-4-yl)urea, 1,1-dimethyl-3-(7-hydroxy-4,5,6,7-tetrahydrobenzo[b]thien-4-yl)urea, 1-methoxy-3-(7-hydroxy-4,5,6,7-tetrahydrobenzo[b]thien-4-yl)urea, 1-methyl-1-methoxy-3-(7-hydroxy-4,5,6,7-tetrahydrobenzo[b]thien-4-yl)urea, 1-hydroxy-3-(7-hydroxy-4,5,6,7-tetrahydrobenzo[b]thien-4-yl)urea, 1-hydroxy-1-methyl-3-(7-hydroxy-4,5,6,7-tetrahydrobenzo[b]thien-4-yl)urea, 1-methoxymethyl-3-(7-hydroxy-4,5,6,7-tetrahydrobenzo[b]thien-4-yl)urea, 1-allyl-3-(7-hydroxy-4,5,6,7-tetrahydrobenzo[b]thien-4-yl)urea, and 1-(2-propynyl)-3-(7-hydroxy-4,5,6,7-tetrahydrobenzo[b]thien-4-yl)urea.

EXAMPLE 67

Preparation of 4,5,6,7-tetrahydrobenzo[b]thien-4-ylurea

A sample of 6,7-dihydrobenzo[b]thiophene is stirred in the cold in 96% sulfuric acid containing 4–6 mole equivalents of urea. After 1 hour the mixture is poured on ice and the organic phase is removed. Evaporation of the organic phase to dryness in vacuo affords 4,5,6,7-tetrahydrobenzo[b]thien-4-ylurea.

EXAMPLE 68

Preparation of 4,5,6,7-tetrahydrobenzo[b]thien-4-ylurea

A 1 gram sample of 4-hydroxy-4,5,6,7-tetrahydrobenzo[b]thiophene is stirred in the cold for several hours in thionyl chloride (5 ml.) and the mixture is evaporated to dryness. The crude 4-chloro-4,5,6,7-tetrahydrobenzo[b]thiophene is then added to a mixture of urea (1–5 mole-equivalents) in dimethylformamide and diisopropyl ethylamine. The mixture is warmed, after several hours, to 50° C. and after 4 hours is poured on ice and the product, 4,5,6,7-tetrahydrobenzo[b]thien-4-ylurea, is collected by filtration.

EXAMPLE 69

Preparation of 4,5,6,7-tetrahydrobenzo[b]thien-4-ylurea

A sample of 6,7-dihydrobenzo[b]thiophene is stirred with silver isocyanate and iodine as described in Example 39 and the resulting product, 5-iodo-4,5,6,7-tetrahydrobenzo[b]thien-4-yl isocyanate is treated with concentrated ammonia solution to afford 5-iodo-4,5,6,7-tetrahydrobenzo[b]thien-4-ylurea. This latter product is then reduced in the manner described in Example 40 to afford 4,5,6,7-tetrahydrobenzo[b]thien-4-ylurea.

The following products set forth in Table XIV below are also obtained by reacting 5-iodo-4,5,6,7-tetrahydrobenzo[b]thien-4-yl isocyanate with $R_2R_3NH$ to afford the corresponding iodo ureas, which are then hydrogenated in the above manner to give compounds of the formula:

TABLE XIV

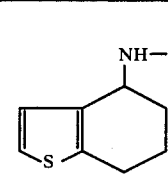

| $R_3$ | $R_2$ |
|---|---|
| H | —$CH_3$ |
| H | —$C_2H_5$ |
| H | —$CH(CH_3)_2$ |
| —$CH_3$ | —$CH_3$ |
| H | —OH |
| H | —$OCH_3$ |
| —$CH_3$ | —OH |
| —$CH_3$ | —$OCH_3$ |

When allyl amine and 2-propynyl amine are used to give 1-allyl- or 1-(2-propynyl)-3-(5-iodo-4,5,6,7-tetrahydrobenzo[b]thien-4-yl)urea, the resulting iodo ureas are deiodinated with tributyl tin hydride ($Bu_3SnH$). This reducing agent ($Bu_3SnH$) can also be used to deiodinate these aforementioned iodo ureas, while use of Zn/HCl gives the desired ureas and polymeric material.

EXAMPLE 70

Preparation of 1-(2-propynyl)-3-(4,5,6,7-tetrahydro-7-oxobenzo[b]thien-4-yl)urea A sample of 11.5 grams of 4,5,6,7-tetrahydro-7-oxobenzo[b]thiophen-4-amine is dissolved in 100 ml. of $CH_2Cl_2$ and the solution is added dropwise over 0.5 hour to 11 grams of carbonyl diimidazole stirred in 50 ml. of $CH_2Cl_2$. The mixture is stirred at room temperature for an hour and then added over a 0.5 hour period to 3.74 grams of 2-propargylamine in 50 ml. of $CH_2Cl_2$. After 3 hours, the crude title product is collected to afford 9.8 grams, m.p. 170°–183° C. Recrystallization from acetone-hexane gives 4.1 grams of title compound, m.p. 197°–199° C.

Similarly, when thiocarbonyl diimidazole is used instead of carbonyl diimidazole, the corresponding 1-(2-propynyl)-3-(4,5,6,7-tetrahydro-7-oxobenzo[b]thien-4-yl)thiourea is obtained.

When the 1-(1-imidazolyl)-3-(4,5,6,7-tetrahydro-7-oxobenzo[b]) thien-4-yl)urea is allowed to react with methyl methoxyamine, the product is 1-methoxy-1-methyl-3-(4,5,6,7-tetrahydro-7-oxobenzo[b]thien-4-yl)urea, m.p. 130°–136° C.

Other amines ($R_2R_3NH$) are used in the same manner to prepare the corresponding ureido compounds as listed in Table XV below. Unless otherwise indicated in Table XV, the products were isolated as the dl-racemates.

TABLE XV

| $R_3$ | $R_2$ | Melting point in degrees C. |
|---|---|---|
| H | —$CH_2$—CH=$CH_2$ | 171–174 |
| H | —$OCH_3$ | 185–188.5 |
| H | -iso-$C_3H_7$ | 198–200 |

TABLE XV-continued

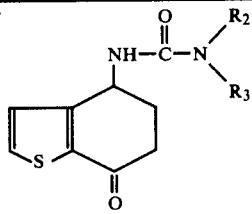

| R3 | R2 | Melting point in degrees C. |
|---|---|---|
| —CH3 | —CH3 | 195–197 |
| —CH3 | —OCH3 | 126–129 |
| —CH3 | —OH | 163–165.5 |
| H | -n-C8H17 | 105–108 |
| H | -C(O)-C6H5 | 204–207 |
| H | H (dextrorotatory enantiomorph) | 243–246 |
| H | H (levorotatory enantiomorph) | 247–249.5 |
| | 4,5,6,7-tetrahydro-2-bromo-7-oxobenzo[b]thien-4-ylurea | 252–253 |
| H | n-C10H21 | 104–107 |
| H | n-C12H25 | 83–86, 116–118 |
| H | n-C14H28 | 88–90. 114–116 |

EXAMPLE 71

Herbicidal Activity

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 11.2 kg per hectare of test compound per cup. The treated cups are then placed on greenhouse benches, watered and cared for in accordance with conventional greenhouse procedures. About four weeks after treatment, the tests are terminated and each cup is examined and rated according to the rating system set forth below. The herbicidal proficiency of the active ingredients of the present invention is evident from the test results which are reported in Table XVI below.

| Rating System: | % Difference in Growth from the Check* |
|---|---|
| 0-No effect | 0 |
| 1-Possible effect | 1–10 |
| 2-Slight effect | 11–25 |
| 3-Moderate effect | 26–40 |
| 5-Definite injury | 41–60 |
| 6-Herbicidal effect | 61–75 |
| 7-Good herbicidal effect | 76–90 |
| 8-Approaching complete kill | 91–99 |
| 9-Complete kill | 100 |
| 4-Abnormal growth, that is, a definite physiological malformation but with an over-all effect less than a 5 on the rating scale. | |

*Based on visual determination of stand, size, vigor, chlorosis, growth malformation and over-all plant appearance.

Plant Abbreviations

SE—Sesbania (*Sesbania exaltata*)
LA—Lambsquarters (*Chenopodium album*)
MU—Mustard (*Brassica kaber*)
PI—Pigweed (*Amaranthus retroflexus*)
RW—Ragweed (*Ambrosia artemisiifolia*)
MG—Morningglory (*Ipomoea purpurea*)
BA—Barnyardgrass (*Echinochloa crusgalli*)
CR—Crabgrass (*Digitaria sanguinalis*)
FO—Green foxtail (*Setaria viridis*)
WO—Wild oats (*Avena fatua*)
TW—Teaweed (*Sida spinosa*)
VL—Velvetleaf (*Abutilon theophrasti*)

TABLE XVI

Preemergence Herbicidal Activity

| Compound | Rate kg/ha | SE | LA | MU | PI | RW | MG | BA | CR | FO | WO | TW | VL |
|---|---|---|---|---|---|---|---|---|---|---|---|---|---|
| 4,5,6,7-Tetrahydrobenzo[b]thien-4-yl-urea | 11.2 | — | 8 | 9 | 2 | 0 | 5 | 9 | 9 | 9 | 0 | — | 9 |
| (−)-4,5,6,7-Tetrahydrobenzo[b]thien-4-yl-urea | 11.2 | 9 | — | 0 | 0 | 9 | 7 | 9 | 9 | 9 | 5 | 7 | 9 |
| (+)-4,5,6,7-Tetrahydrobenzo[b]thien-4-yl-urea | 11.2 | 0 | — | 9 | 8 | 6 | 4 | 8 | 9 | 8 | 0 | 1 | 2 |
| 1-Ethyl-3-(4,5,6,7-tetrahydrobenzo[b]-thien-4-yl-urea | 11.2 | — | 9 | 8 | 8 | 0 | 3 | 6 | 7 | 6 | 3 | 8 | 7 |
| 2-Chloro-4,5,6,7-tetrahydrobenzo[b]thien-4-yl-urea | 11.2 | — | 9 | 9 | 8 | 9 | 0 | 7 | 9 | 9 | 0 | 0 | 0 |
| 1,1-Dimethyl-3-(4,5,6,7-tetrahydrobenzo[b]-thien-4-yl)urea | 11.2 | — | 8 | 9 | 6 | 7 | 9 | 2 | 7 | 2 | 7 | 9 | 9 |
| N-(4,5,6,7-Tetrahydrobenzo[b]thien-4-yl)-1-pyrrolidinecarboxamide | 11.2 | — | 9 | 9 | 9 | 9 | 9 | 7 | 8 | 9 | 6 | 9 | 9 |
| N-(4,5,6,7-Tetrahydrobenzo[b]thien-4-yl)-1-piperidinecarboxamide | 11.2 | — | 7 | 6 | 0 | 9 | 0 | 5 | 9 | 9 | 0 | — | 9 |
| 1-(4,5,6,7-Tetrahydrobenzo[b]thien-4-yl)-2-thiourea | 11.2 | — | 0 | 0 | 0 | 0 | 0 | 7 | 8 | 7 | 0 | — | 3 |
| N-(4,5,6,7-Tetrahydrobenzo[b]thien-4-yl)-thio-1-piperidinecarboxamide | 11.2 | — | 0 | 0 | 0 | 0 | 0 | 8 | 8 | 8 | 0 | — | 0 |
| 1-(Methoxymethyl)-3-(4,5,6,7-tetrahydrobenzo[b]thien-4-yl)urea | 11.2 | 9 | | 7 | 0 | 0 | 1 | 9 | 9 | 9 | 3 | 4 | 7 |
| 1-(Benzyloxy)-3-(4,5,6,7-tetrahydrobenzo-[b]thien-4-yl)urea | 11.2 | 0 | — | 9 | 9 | 9 | 0 | 0 | 0 | 5 | 0 | 2 | 2 |
| 1-Allyl-3-(4,5,6,7-tetrahydrobenzo[b]-thien-4-yl)urea | 11.2 | — | 8 | 7 | 5 | 0 | 0 | 3 | 7 | 3 | 0 | 0 | 0 |
| 1-Ethoxy-3-(4,5,6,7-tetrahydrobenzo[b]-thien-4-yl)urea | 11.2 | 5 | — | 5 | 8 | 3 | 8 | 7 | 7 | 6 | 1 | 9 | 9 |
| 1-(2-Propynyl)-3-(4,5,6,7-tetrahydrobenzo- | 11.2 | — | 9 | 2 | 8 | 0 | 7 | 0 | 7 | 6 | 0 | 2 | 2 |

TABLE XVI-continued

| | | Preemergence Herbicidal Activity | | | | | | | | | | | |
|---|---|---|---|---|---|---|---|---|---|---|---|---|---|
| Compound | Rate kg/ha | SE | LA | MU | PI | RW | MG | BA | CR | FO | WO | TW | VL |
| [b]thien-4-yl)urea | | | | | | | | | | | | | |
| 1-Methyl-1-(2-propynyl)-3-(4,5,6,7-tetra-hydrobenzo[b]thien-4-yl)urea | 11.2 | 8 | — | 9 | 9 | 4 | 4 | 8 | 8 | 9 | 3 | 9 | 9 |
| 1,1-Diallyl-3-(4,5,6,7-tetrahydrobenzo[b]4-yl)urea | 11.2 | 0 | — | 8 | 8 | 0 | 0 | 6 | 8 | 7 | 1 | 9 | 9 |
| 1-(4,5,6,7-Tetrahydrobenzo[b]thien-4-yl)-3-(2-thienyl)urea | 11.2 | 6 | — | 9 | 9 | 0 | 0 | 7 | 8 | 7 | 0 | 7 | 9 |
| 1-Methyl-3-(4,5,6,7-tetrahydrobenzo[b]-thien-7-yl)urea | 11.2 | 9 | — | 9 | 9 | 9 | 9 | 7 | 8 | 7 | 6 | 9 | 9 |
| 1-Benzyl-1-methyl-3-(4,5,6,7-tetrahydro-benzo[b]thien-4-yl)urea | 11.2 | 0 | — | 8 | 0 | 0 | 0 | 7 | 6 | 6 | 0 | 9 | 6 |
| 1-Acetyl-3-(4,5,6,7-tetrahydrobenzo[b]thien-4-yl)urea | 11.2 | 5 | — | 8 | 9 | 0 | 2 | 9 | 9 | 7 | 2 | 5 | 8 |
| 1-(4,5,6,7-Tetrahydrobenzo[b]thien-4-yl)-3-trichloroacetyl)urea | 11.2 | 0 | — | 0 | 2 | 0 | 8 | 9 | 9 | 9 | 4 | 6 | 6 |
| 1-(4,5,6,7-Tetrahydro-7-oxobenzo[b]thien-4-yl)-3-trichloroacetyl-urea | 11.2 | 0 | — | 0 | 1 | 0 | 8 | 9 | 9 | 9 | 8 | 0 | 4 |

EXAMPLE 72

Preparation of 1-(methoxymethyl)-3-(4,5,6,7-tetrahydro-7-hydroxybenzo[b]thien-4-yl)urea A mixture of 4,5,6,7-tetrahydro-7-hydroxybenzo[b]-thien-4-yl urea (4 g., 18.87 mmole), sodium hydroxide (0.969 g., 24.22 mmole), paraformaldehyde (1.038 g., 34.6 mmole) and methanol (94 ml.) is stirred and heated at reflux under a nitrogen atmosphere for 23 hours. The mixture is allowed to cool and excess solid carbon dioxide is added. Evaporation in vacuo affords a solid which is stirred with water (50 ml.) for 2 hours, filtered and air dried to furnish 3.16 g. of the title compound (65% yield) m.p. 157°–159° C. dec. Recrystallization from hot acetone gives the analytical specimen 160°–161° C. dec.

EXAMPLE 73

Preparation of 1-(methoxymethyl)-3-(4,5,6,7-tetrahydro-7-oxobenzo[b]thien-4-yl)urea A solution of 1-(methoxymethyl)-3-(4,5,6,7-tetrahydro-7-hydroxybenzo[b]thien-4-yl)urea (0.35 g., 1.37 mmole) in acetone (40 ml.) is treated with manganese dioxide (3.5 g.). After 2 hours stirring the reaction mixture is filtered through celite, the cake washed thoroughly with acetone and the filtrate and washings evaporated to furnish 0.32 g. on 90.7% yield of the title compound as a crystalline solid, m.p. 155°–158° C. Recrystallization from hot acetone affords the analytical sample, m.p. 159°–162° C.

I claim:

1. A compound selected from the group consisting of those of the formulae:

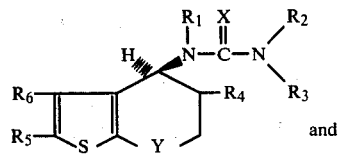
and
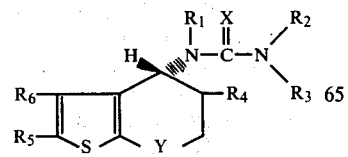

wherein X is oxygen or sulfur; Y is a divalent radical selected from the group consisting of those of the formulae:

$R_1$ is hydrogen or alkyl $C_1$–$C_4$; $R_3$ is selected from the group consisting of hydrogen, alkyl $C_1$–$C_4$, cycloalkyl $C_3$–$C_6$, allyl, 2-propynyl, benzyl and β-phenethyl; $R_4$ is hydrogen or alkyl $C_1$–$C_4$; $R_5$ is hydrogen, chloro, bromo or iodo; $R_6$ is hydrogen or alkyl $C_1$–$C_4$; $R_2$ is selected from the group consisting of the substituents listed in the following table:

hydrogen
alkyl $C_1$—$C_{12}$
cycloalkyl $C_3$—$C_6$
allyl
methallyl
2-butenyl
2-propynyl
hydroxy
alkoxy $C_1$—$C_6$
allyloxy
methallyloxy
2-butenyloxy
methoxymethyl
phenoxy
—CH$_2$—CH$_2$—OH
—CH$_2$—CH$_2$—O—CH$_3$
—CH$_2$—CH$_2$—S—CH$_3$
—CH$_2$—CH(OR)$_2$
—CH$_2$—CF$_3$
—CH$_2$—CN
—CH$_2$—CO$_2$R
—NH—CO$_2$R $$-\overset{O}{\underset{\|}{C}}-R$$

$$-\overset{O}{\underset{\|}{C}}-CCl_3$$

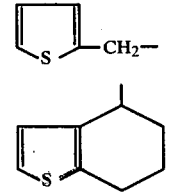

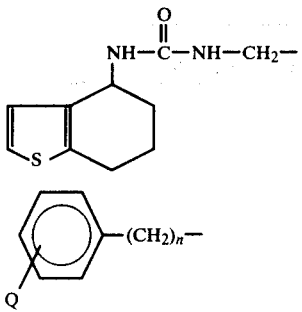

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

2. The compound according to claim 1 selected from the group consisting of the dextrorotatory enantiomorph, the levorotatory enantiomorph, and the racemic mixture thereof of a compound of the formula:

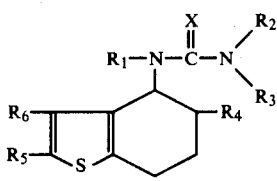

wherein X is oxygen or sulfur; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and β-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

hydrogen
alkyl $C_1$—$C_{12}$
cycloalkyl $C_3$—$C_6$
allyl
methallyl
2-butenyl
2-propynyl
hydroxy
alkoxy $C_1$—$C_6$
allyloxy
methallyloxy
2-butenyloxy
methoxymethyl
phenoxy
—$CH_2$—$CH_2$—OH
—$CH_2$—$CH_2$—O—$CH_3$
—$CH_2$—$CH_2$—S—$CH_3$
—$CH_2$—$CH(OR)_2$
—$CH_2$—$CF_3$
—$CH_2$—CN
—$CH_2$—$CO_2R$ —NH—$CO_2R$
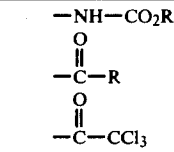
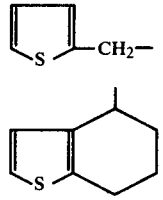
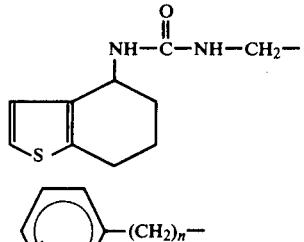

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

3. The racemic mixture according to claim 2 wherein X is oxygen and $R_1$, $R_2$, $R_3$, $R_4$, $R_5$ and $R_6$ are hydrogen; dl-4,5,6,7-tetrahydrobenzo[b]thien-4-ylurea.

4. The dextrorotatory enantiomorph according to claim 2 wherein X is oxygen and $R_1$, $R_2$, $R_3$, $R_4$, $R_5$ and $R_6$ are hydrogen; d-4,5,6,7-tetrahydrobenzo[b]thien-4-ylurea.

5. The levorotatory enantiomorph according to claim 2 wherein X is oxygen and $R_1$, $R_2$, $R_3$, $R_4$, $R_5$ and $R_6$ are hydrogen, l-4,5,6,7-tetrahydrobenzo[b]thien-4-ylurea.

6. The racemic mixture according to claim 2 wherein X is oxygen, $R_1$ and $R_2$ are hydrogen, $R_3$ is methyl, and $R_4$, $R_5$ and $R_6$ are hydrogen; dl-1-methyl-3-(4,5,6,7-tetrahydrobenzo[b]thien-4-yl)urea.

7. The racemic mixture according to claim 2 wherein X is oxygen, $R_1$ is hydrogen, $R_2$ is methoxy, $R_3$ is methyl, and $R_4$, $R_5$ and $R_6$ are hydrogen; dl-1-methoxy-1-methyl-3-(4,5,6,7-tetrahydrobenzo[b]thien-4-yl)urea.

8. The racemic mixture according to claim 2 wherein X is oxygen, $R_1$ and $R_2$ are hydrogen, $R_3$ is ethyl, and $R_4$, $R_5$ and $R_6$ are hydrogen; dl-1-ethyl-3-(4,5,6,7-tetrahydrobenzo[b]thien-4-yl)urea.

9. The racemic mixture according to claim 2 wherein X is oxygen, $R_1$ is hydrogen, $R_2$ is methoxy, and $R_3$, $R_4$, $R_5$ and $R_6$ are hydrogen; dl-1-methoxy-3-(4,5,6,7-tetrahydrobenzo[b]thien-4-yl)urea.

10. The racemic mixture according to claim 2 wherein X is oxygen, $R_1$ is hydrogen, $R_2$ is hydroxy, $R_3$ is methyl, and $R_4$, $R_5$ and $R_6$ are hydrogen; dl-1-hydroxy-1-methyl-3-(4,5,6,7-tetrahydrobenzo[b]thien-4-yl)urea.

11. The racemic mixture according to claim 2 wherein X is oxygen, $R_1$ is hydrogen; $R_2$ is hydroxy, and $R_3$, $R_4$, $R_5$ and $R_6$ are hydrogen; dl-1-hydroxy-3-(4,5,6,7-tetrahydrobenzo[b]thien-4-yl)urea.

12. The racemic mixture according to claim 2 wherein X is oxygen, $R_1$ is hydrogen; $R_2$ is methoxymethyl, and $R_3$, $R_4$, $R_5$ and $R_6$ are hydrogen; dl-1-methoxymethyl-3-(4,5,6,7-tetrahydrobenzo[b]thien-4-yl)urea.

13. The racemic mixture according to claim 2 wherein X is oxygen, $R_1$ and $R_2$ are hydrogen, $R_3$ is 2-propynyl, and $R_4$, $R_5$ and $R_6$ are hydrogen; dl-1-(2-propynyl)-3-(4,5,6,7-tetrahydrobenzo[b]thien-4-yl)urea.

14. The racemic mixture according to claim 2 wherein X is oxygen, $R_1$ and $R_2$ are hydrogen, $R_3$ is allyl, and $R_4$, $R_5$ and $R_6$ are hydrogen; dl-1-allyl-3-(4,5,6,7-tetrahydrobenzo[b]thien-4-yl)urea.

15. The racemic mixture according to claim 2 wherein X is oxygen, $R_1$ and $R_2$ are hydrogen, $R_3$ is isopropyl, and $R_4$, $R_5$ and $R_6$ are hydrogen; dl-1-isopropyl-3-(4,5,6,7-tetrahydrobenzo[b]thien-4-yl)urea.

16. The racemic mixture according to claim 2 wherein X is oxygen, $R_1$ is hydrogen, $R_2$ and $R_3$ are methyl, and $R_4$, $R_5$ and $R_6$ are hydrogen; dl-1,1-dimethyl-3-(4,5,6,7-tetrahydrobenzo[b]thien-4-yl)urea.

17. The compound according to claim 1 selected from the group consisting of the dextrorotatory enantiomorph, the levorotatory enantiomorph, and the racemic mixture thereof of a compound of the formula:

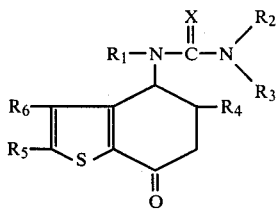

wherein X is oxygen or sulfur; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and β-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

hydrogen
alkyl $C_1$—$C_{12}$
cycloalkyl $C_3$—$C_6$
allyl
methallyl
2-butenyl
2-propynyl
hydroxy
alkoxy $C_1$—$C_6$
allyloxy
methallyloxy
2-butenyloxy
methoxymethyl
phenoxy
—CH$_2$—CH$_2$—OH
—CH$_2$—CH$_2$—O—CH$_3$
—CH$_2$—CH$_2$—S—CH$_3$
—CH$_2$—CH(OR)$_2$
—CH$_2$—CF$_3$
—CH$_2$—CN
—CH$_2$—CO$_2$R
—NH—CO$_2$R

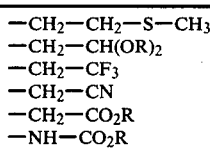

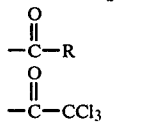

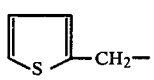

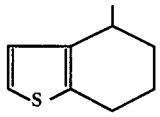

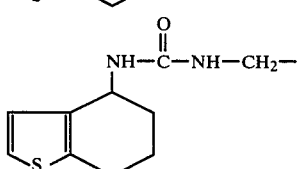

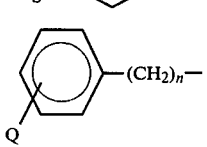

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

18. The racemic mixture according to claim 17 wherein X is oxygen and $R_1$, $R_2$, $R_3$, $R_4$, $R_5$ and $R_6$ are hydrogen; dl-4,5,6,7-tetrahydro-7-oxobenzo[b]thien-4-ylurea.

19. The dextrorotatory enantiomorph according to claim 17 wherein X is oxygen and $R_1$, $R_2$, $R_3$, $R_4$, $R_5$ and $R_6$ are hydrogen; d-4,5,6,7-tetrahydro-7-oxobenzo[b]thien-4-ylurea.

20. The levorotatory enantiomorph according to claim 17 wherein X is oxygen and $R_1$, $R_2$, $R_3$, $R_4$, $R_5$ and $R_6$ are hydrogen; l-4,5,6,7-tetrahydro-7-oxobenzo[b]thien-4-ylurea.

21. The racemic mixture according to claim 17 wherein X is oxygen, $R_1$ and $R_2$ are hydrogen, $R_3$ is methyl, and $R_4$, $R_5$ and $R_6$ are hydrogen; dl-1-methyl-3-(4,5,6,7-tetrahydro-7-oxobenzo[b]thien-4-yl)urea.

22. The racemic mixture according to claim 17 wherein X is oxygen, $R_1$ and $R_2$ are hydrogen, $R_3$ is ethyl, and $R_4$, $R_5$ and $R_6$ are hydrogen; dl-1-ethyl-3-(4,5,6,7-tetrahydro-7-oxobenzo[b]thien-4-yl)urea.

23. The racemic mixture according to claim 17 wherein X is oxygen, $R_1$ is hydrogen, $R_2$ is methoxymethyl, and $R_3$, $R_4$, $R_5$ and $R_6$ are hydrogen; dl-1-methoxymethyl-3-(4,5,6,7-tetrahydro-7-oxobenzo[b]thien-4-yl)urea.

24. The racemic mixture according to claim 17 wherein X is oxygen, $R_1$ and $R_2$ are hydrogen, $R_3$ is 2-propynyl, and $R_4$, $R_5$ and $R_6$ are hydrogen; dl-1-(2-propynyl)-3-(4,5,6,7-tetrahydro-7-oxobenzo[b]thien-4-yl)urea.

25. The racemic mixture according to claim 17 wherein X is oxygen, $R_1$ and $R_2$ are hydrogen, $R_3$ is allyl, and $R_4$, $R_5$ and $R_6$ are hydrogen; dl-1-allyl-3-(4,5,6,7-tetrahydro-7-oxobenzo[b]thien-4-yl)urea.

26. The racemic mixture according to claim 17 wherein X is oxygen, $R_1$ is hydrogen, $R_2$ is methoxy, $R_3$ is methyl, and $R_4$, $R_5$ and $R_6$ are hydrogen, dl-1-methoxy-1-methyl-3-(4,5,6,7-tetrahydro-7-oxobenzo[b]thien-4-yl)urea.

27. The racemic mixture according to claim 17 wherein X is oxygen, $R_1$ is hydrogen, $R_2$ is hydroxy and $R_3$, $R_4$, $R_5$ and $R_6$ are hydrogen; dl-1-hydroxy-3-(4,5,6,7-tetrahydro-7-oxobenzo[b]thien-4-yl)urea.

28. The racemic mixture according to claim 17 wherein X is oxygen, $R_1$ is hydrogen, $R_2$ is hydroxy, $R_3$ is methyl, and $R_4$, $R_5$ and $R_6$ are hydrogen; dl-1-hydroxy-1-methyl-3-(4,5,6,7-tetrahydro-7-oxobenzo[b]thien-4-yl)urea.

29. The racemic mixture according to claim 17 wherein X is oxygen, $R_1$ is hydrogen, $R_2$ is methoxy, and $R_3$, $R_4$, $R_5$ and $R_6$ are hydrogen; dl-1-methoxy-3-(4,5,6,7-tetrahydro-7-oxobenzo[b]thien-4-yl)urea.

30. The racemic mixture according to claim 17 wherein X is oxygen, $R_1$ is hydrogen, $R_2$ and $R_3$ are methyl, and $R_4$, $R_5$ and $R_6$ are hydrogen; dl-1,1-dimethyl-3-(4,5,6,7-tetrahydro-7-oxobenzo[b]thien-4-yl)urea.

31. The racemic mixture according to claim 17 wherein X is oxygen, $R_1$ and $R_2$ are hydrogen, $R_3$ is isopropyl, and $R_4$, $R_5$ and $R_6$ are hydrogen; dl-1-isopropyl-3-(4,5,6,7-tetrahydro-7-oxobenzo[b]thien-4-yl)urea.

32. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

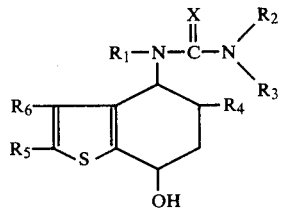

wherein X is oxygen or sulfur; $R_1$ is hydrogen or alkyl $C_1$–$C_4$; $R_3$ is selected from the group consisting of hydrogen, alkyl $C_1$–$C_4$, cycloalkyl $C_3$–$C_6$, allyl, 2-propynyl, benzyl and β-phenethyl; $R_4$ is hydrogen or alkyl $C_1$–$C_4$; $R_5$ is hydrogen, chloro, bromo or iodo; $R_6$ is hydrogen or alkyl $C_1$–$C_4$; $R_2$ is selected from the group consisting of the substituents listed in the following table:

hydrogen
alkyl $C_1$—$C_{12}$

-continued cycloalkyl $C_3$—$C_6$
allyl
methallyl
2-butenyl
2-propynyl
hydroxy
alkoxy $C_1$—$C_6$
allyloxy
methallyloxy
2-butenyloxy
methoxymethyl
phenoxy
—$CH_2$—$CH_2$—OH
—$CH_2$—$CH_2$—O—$CH_3$
—$CH_2$—$CH_2$—S—$CH_3$
—$CH_2$—CH(OR)$_2$
—$CH_2$—$CF_3$
—$CH_2$—CN
—$CH_2$—$CO_2$R
—NH—$CO_2$R $$-\overset{O}{\underset{\|}{C}}-R$$

$$-\overset{O}{\underset{\|}{C}}-CCl_3$$

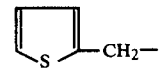

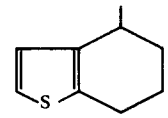

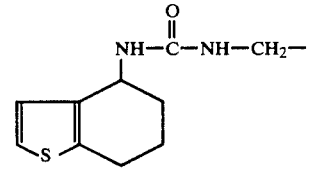

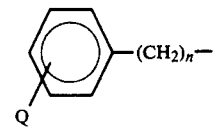

wherein R is lower alkyl, n is 0, 1 or 2, and Q is selected from the group consisting of the substituents listed in the following table:

| n = 0 | n = 1 | n = 2 |
|---|---|---|
| 2-methyl-4-bromo | hydrogen | hydrogen |
|  | 4-chloro |  |
| 3- or 4-methoxy | 4-methoxy |  |
| 4-ethoxy |  |  |
| 4-chloro |  |  |
| 4-butoxy |  |  |
| 4-methylthio |  |  |
| 2,4-dimethyl |  |  |
| 2,4-dichloro |  |  |
| 4-nitro |  |  |

33. The cis-racemic mixture according to claim 32 wherein X is oxygen and $R_1$, $R_2$, $R_3$, $R_4$, $R_5$ and $R_6$ are hydrogen; dl-cis-4,5,6,7-tetrahydro-7-hydroxybenzo[b]thien-4-ylurea.

34. The trans-racemic mixture according to claim 32 wherein X is oxygen and $R_1$, $R_2$, $R_3$, $R_4$, $R_5$ and $R_6$ are hydrogen; dl-trans-4,5,6,7-tetrahydro-7-hydroxybenzo[b]thien-4-ylurea.

35. The cis-dextrorotatory enantiomorph according to claim 32 wherein X is oxygen and $R_1$, $R_2$, $R_3$, $R_4$, $R_5$ and R6 are hydrogen; d-cis-4,5,6,7-tetrahydro-7-hydroxybenzo[b]thien-4-ylurea.

36. The cis-levorotatory enantiomorph according to claim 32 wherein X is oxygen and $R_1$, $R_2$, $R_3$, $R_4$, $R_5$ and $R_6$ are hydrogen; l-cis-4,5,6,7-tetrahydro-7-hydroxybenzo[b]thien-4-ylurea.

37. The trans-dextrorotatory enantiomorph according to claim 32 wherein X is oxygen and $R_1$, $R_2$, $R_3$, $R_4$, $R_5$ and $R_6$ are hydrogen; d-trans-4,5,6,7-tetrahydro-7-hydroxybenzo[b]thien-4-ylurea.

38. The trans-levorotatory enantiomorph according to claim 32 wherein X is oxygen and $R_1$, $R_2$, $R_3$, $R_4$, $R_5$ and $R_6$ are hydrogen; l-trans-4,5,6,7-tetrahydro-7-hydroxybenzo[b]thien-4-ylurea.

39. The cis-racemic mixture according to claim 32 wherein X is oxygen, $R_1$ and $R_2$ are hydrogen, $R_3$ is methyl, and $R_4$, $R_5$ and $R_6$ are hydrogen; dl-cis-1-methyl-3-(4,5,6,7-tetrahydro-7-hydroxybenzo[b]thien-4-yl)urea.

40. The trans-racemic mixture according to claim 32 wherein X is oxygen, $R_1$ and $R_2$ are hydrogen, $R_3$ is methyl, and $R_4$, $R_5$ and $R_6$ are hydrogen; dl-trans-1-methyl-3-(4,5,6,7-tetrahydro-7-hydroxybenzo[b]thien-4-yl)urea.

41. The cis-racemic mixture according to claim 32 wherein X is oxygen, $R_1$ and $R_2$ are hydrogen, $R_3$ is ethyl, and $R_4$, $R_5$ and $R_6$ are hydrogen; dl-cis-1-ethyl-3-(4,5,6,7-tetrahydro-7-hydroxybenzo[b]thien-4-yl)urea.

42. The trans-racemic mixture according to claim 32 wherein X is oxygen, $R_1$ and $R_2$ are hydrogen, $R_3$ is ethyl, and $R_4$, $R_5$ and $R_6$ are hydrogen; dl-trans-1-ethyl-3-(4,5,6,7-tetrahydro-7-hydroxybenzo[b]thien-4-yl)urea.

43. The cis-racemic mixture according to claim 32 wherein X is oxygen, $R_1$ is hydrogen, $R_2$ and $R_3$ are methyl, and $R_4$, $R_5$ and $R_6$ are hydrogen; dl-cis-1,1-dimethyl-3-(4,5,6,7-tetrahydro-7-hydroxybenzo[b]thien-4-yl)urea.

44. The trans-racemic mixture according to claim 32 wherein X is oxygen, $R_1$ is hydrogen, $R_2$ and $R_3$ are methyl, and $R_4$, $R_5$ and $R_6$ are hydrogen; dl-trans-1,1-dimethyl-3-(4,5,6,7-tetrahydro-7-hydroxybenzo[b]thien-4-yl)urea.

45. The cis-racemic mixture according to claim 32 wherein X is oxygen, $R_1$ is hydrogen, $R_2$ is methoxymethyl, and $R_3$, $R_4$, $R_5$ and $R_6$ are hydrogen; dl-cis-1-methoxymethyl-3-(4,5,6,7-tetrahydro-7-hydroxybenzo[b]thien-4-yl)urea.

46. The trans-racemic mixture according to claim 32 wherein X is oxygen, $R_1$ is hydrogen, $R_2$ is methoxymethyl, and $R_3$, $R_4$, $R_5$ and $R_6$ are hydrogen; dl-trans-1-methoxymethyl-3-(4,5,6,7-tetrahydro-7-hydroxybenzo[b]thien-4-yl)urea.

47. The cis-racemic mixture according to claim 32 wherein X is oxygen, $R_1$ and $R_2$ are hydrogen, $R_3$ is isopropyl, and $R_4$, $R_5$ and $R_6$ are hydrogen; dl-cis-1-isopropyl-3-(4,5,6,7-tetrahydro-7-hydroxybenzo[b]thien-4-yl)urea.

48. The trans-racemic mixture according to claim 32 wherein X is oxygen, $R_1$ and $R_2$ are hydrogen, $R_3$ is isopropyl, and $R_4$, $R_5$ and $R_6$ are hydrogen; dl-trans-1-isopropyl-3-(4,5,6,7-tetrahydro-7-hydroxybenzo[b]thien-4-yl)urea.

49. The cis-racemic mixture according to claim 32 wherein X is oxygen, $R_1$ and $R_2$ are hydrogen, $R_3$ is 2-propynyl, and $R_4$, $R_5$ and $R_6$ are hydrogen; dl-cis-1-(2-propynyl)-3-(4,5,6,7-tetrahydro-7-hydroxybenzo[b]thien-4-yl)urea.

50. The trans-racemic mixture according to claim 32 wherein X is oxygen, $R_1$ and $R_2$ are hydrogen, $R_3$ is 2-propynyl, and $R_4$, $R_5$ and $R_6$ are hydrogen; dl-trans-1-(2-propynyl)-3-(4,5,6,7-tetrahydro-7-hydroxybenzo[b]thien-4-yl)urea.

51. The cis-racemic mixture according to claim 32 wherein X is oxygen, $R_1$ and $R_2$ are hydrogen, $R_3$ is allyl, and $R_4$, $R_5$ and $R_6$ are hydrogen; dl-cis-1-allyl-3-(4,5,6,7-tetrahydro-7-hydroxybenzo[b]thien-4-yl)urea.

52. The trans-racemic mixture according to claim 32 wherein X is oxygen, $R_1$ and $R_2$ are hydrogen, $R_3$ is allyl, and $R_4$, $R_5$ and $R_6$ are hydrogen; dl-trans-1-allyl-3-(4,5,6,7-tetrahydro-7-hydroxybenzo[b]thien-4-yl)urea.

53. The cis-racemic mixture according to claim 32 wherein X is oxygen, $R_1$ is hydrogen, $R_2$ is methoxy, and $R_3$, $R_4$, $R_5$ and $R_6$ are hydrogen; dl-cis-1-methoxy-3-(4,5,6,7-tetrahydro-7-hydroxybenzo[b]thien-4-yl)urea.

54. The trans-racemic mixture according to claim 32 wherein X is oxygen, $R_1$ is hydrogen, $R_2$ is methoxy, and $R_3$, $R_4$, $R_5$ and $R_6$ are hydrogen; dl-trans-1-methoxy-3-(4,5,6,7-tetrahydro-7-hydroxybenzo[b]thien-4-yl)urea.

55. The cis-racemic mixture according to claim 32 wherein X is oxygen, $R_1$ is hydrogen, $R_2$ is methoxy, $R_3$ is methyl, and $R_4$, $R_5$ and $R_6$ are hydrogen; dl-cis-1-methoxy-1-methyl-3-(4,5,6,7-tetrahydro-7-hydroxybenzo[b]thien-4-yl)urea.

56. The trans-racemic mixture according to claim 32 wherein X is oxygen, $R_1$ is hydrogen, $R_2$ is methoxy, $R_3$ is methyl, and $R_4$, $R_5$ and $R_6$ are hydrogen; dl-trans-1-methoxy-1-methyl-3-(4,5,6,7-tetrahydro-7-hydroxybenzo[b]thien-4-yl)urea.

57. The cis-racemic mixture according to claim 32 wherein X is oxygen, $R_1$ is hydrogen, $R_2$ is hydroxy, and $R_3$, $R_4$, $R_5$ and $R_6$ are hydrogen; dl-cis-1-hydroxy-3-(4,5,6,7-tetrahydro-7-hydroxybenzo[b]thien-4-yl)urea.

58. The trans-racemic mixture according to claim 32 wherein X is oxygen, $R_1$ is hydrogen, $R_2$ is hydroxy, and $R_3$, $R_4$, $R_5$ and $R_6$ are hydrogen; dl-trans-1-hydroxy-3-(4,5,6,7-tetrahydro-7-hydroxybenzo[b]thien-4-yl)urea.

59. The cis-racemic mixture according to claim 32 wherein X is oxygen, $R_1$ is hydrogen, $R_2$ is hydroxy, $R_3$ is methyl, and $R_4$, $R_5$ and $R_6$ are hydrogen; dl-cis-1-hydroxy-1-methyl-3-(4,5,6,7-tetrahydro-7-hydroxybenzo[b]thien-4-yl)urea.

60. The trans-racemic mixture according to claim 32 wherein X is oxygen, $R_1$ is hydrogen, $R_2$ is hydroxy, $R_3$ is methyl, and $R_4$, $R_5$ and $R_6$ are hydrogen; dl-trans-1-hydroxy-1-methyl-3-(4,5,6,7-tetrahydro-7-hydroxybenzo[b]thien-4-yl)urea.

61. A compound selected from the group consisting of the dextrorotatory enantiomorph, the levorotatory enantiomorph, and the racemic mixture thereof of a compound of the formula, according to claim 1:

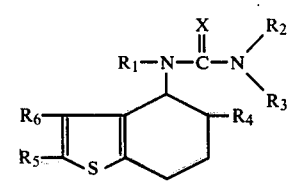

wherein X is oxygen or sulfur; $R_1$ is hydrogen or alkyl $C_1$–$C_4$; $R_3$ is selected from the group consisting of hydrogen, alkyl $C_1$–$C_4$, cycloalkyl $C_3$–$C_6$, allyl, 2-propynyl, benzyl and β-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

hydrogen
alkyl $C_1$-$C_8$
cycloalkyl $C_3$-$C_6$
allyl
methallyl
2-butenyl
2-propynyl
hydroxy
alkoxy $C_1$-$C_6$
allyloxy
methallyloxy
2-butenyloxy
methoxymethyl
phenoxy
—$CH_2$—$CH_2$—OH
—$CH_2$—$CH(OR)_2$
—$CH_2$—$CF_3$
—$CH_2$—CN
—NH—$CO_2$R $$-\overset{O}{\underset{\|}{C}}-R$$

$$-\overset{O}{\underset{\|}{C}}-CCl_3$$

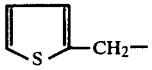

wherein R is lower alkyl, n is 0, 1 or 2, and Q is selected from the group consisting of the substituents listed in the following table:

| n = 0 | n = 1 | n = 2 |
|---|---|---|
| 4-chloro | hydrogen | hydrogen |
| 3- or 4-methoxy | 4-methoxy | |
| 4-ethoxy | | |
| 4-butoxy | | |
| 4-methylthio | | |
| 2,4-dimethyl | | |
| 2,4-dichloro | | |
| 2,4-dichloro | | |
| 4-nitro | | |
| 2-methyl-4-bromo | | |

62. The compound according to claim 1 selected from the group consisting of the dextrorotatory enantiomorph, the levorotatory enantiomorph, and the racemic mixture thereof of a compound of the formula:

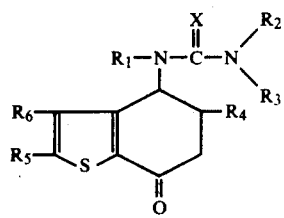

wherein X is oxygen or sulfur; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and β-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

hydrogen
alkyl $C_1$-$C_8$
cycloalkyl $C_3$-$C_6$
allyl
methallyl
2-butenyl
2-propynyl
hydroxy
alkoxy $C_1$-$C_6$
allyloxy
methallyloxy
2-butenyloxy
methoxymethyl
phenoxy
—$CH_2$—$CH_2$—OH
—$CH_2$—$CH(OR)_2$
—$CH_2$—$CF_3$
—$CH_2$—CN
—NH—$CO_2$R $$-\overset{O}{\underset{\|}{C}}-R$$

$$-\overset{O}{\underset{\|}{C}}-CCl_3$$

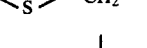

wherein R is lower alkyl, n is 0, 1 or 2, and Q is selected from the group consisting of the substituents listed in the following table:

| n = 0 | n = 1 | n = 2 |
|---|---|---|
| 4-chloro | hydrogen | hydrogen |
| 3- or 4-methoxy | 4-methoxy | |
| 4-ethoxy | | |
| 4-butoxy | | |
| 4-methylthio | | |
| 2,4-dimethyl | | |
| 2,4-dichloro | | |
| 2,4-dichloro | | |
| 4-nitro | | |

| n = 0 | n = 1 | n = 2 |
|---|---|---|
| 2-methyl-4-bromo | | |

63. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

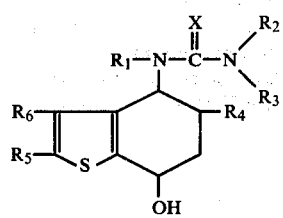

wherein X is oxygen or sulfur; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and $\beta$-phenethyl; $R_4$ is hydrogen or alkyl $C_1$-$C_4$; $R_5$ is hydrogen, chloro, bromo or iodo; $R_6$ is hydrogen or alkyl $C_1$-$C_4$; $R_2$ is selected from the group consisting of the substituents listed in the following table:

| |
|---|
| hydrogen |
| alkyl $C_1$-$C_8$ |
| cycloalkyl $C_3$-$C_6$ |
| allyl |
| methallyl |
| 2-butenyl |
| 2-propynyl |
| hydroxy |
| alkoxy $C_1$-$C_6$ |
| allyloxy |
| methallyloxy |
| 2-butenyloxy |
| methoxymethyl |
| phenoxy |
| —$CH_2$—$CH_2$—OH |
| —$CH_2$—$CH(OR)_2$ |
| —$CH_2$—$CF_3$ |
| —$CH_2$—CN |
| —NH—$CO_2$R |
| $-\overset{O}{\underset{\|}{C}}-R$ |
| $-\overset{O}{\underset{\|}{C}}-CCl_3$ |
| 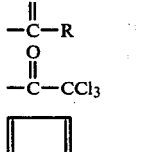  |
| 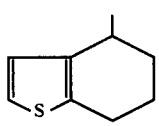 |
| 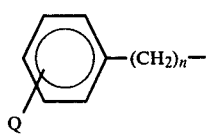 | wherein R is lower alkyl, n is 0, 1 or 2, and Q is selected from the group consisting of the substituents listed in the following table:

| n = 0 | n = 1 | n = 2 |
|---|---|---|
| 4-chloro | hydrogen | hydrogen |
| 3- or 4-methoxy | 4-methoxy | |
| 4-ethoxy | | |
| 4-butoxy | | |
| 4-methylthio | | |
| 2,4-dimethyl | | |
| 2,4-dichloro | | |
| 2,4-dichloro | | |
| 4-nitro | | |
| 2-methyl-4-bromo | | |

64. The compound according to claim 1 selected from the group consisting of the dextrorotatory enantiomorph, the levorotatory enantiomorph, and the racemic mixture thereof of a compound of the formula:

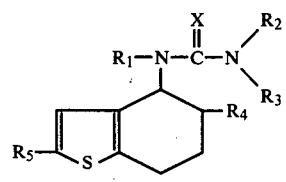

wherein X is oxygen or sulfur; $R_1$ is hydrogen or alkyl $C_1$-$C_4$; $R_3$ is selected from the group consisting of hydrogen, alkyl $C_1$-$C_4$; cycloalkyl $C_3$-$C_6$, allyl, 2-propynyl, benzyl and $\beta$-phenethyl; $R_4$ is hydrogen or alkyl $C_1$-$C_4$; $R_5$ is hydrogen, chloro, bromo or iodo; and $R_2$ is selected from the group consisting of the substituents listed in the following table:

| |
|---|
| hydrogen |
| alkyl $C_1$-$C_8$ |
| cycloalkyl $C_3$-$C_4$ |
| allyl |
| 2-propynyl |
| hydroxy |
| alkoxy $C_1$-$C_6$ |
| methoxymethyl |
| phenoxy |
| 4-methoxyphenyl |

65. The compound according to claim 1 selected from the group consisting of the dextrorotatory enantiomorph, the levorotatory enantiomorph, and the racemic mixture thereof of a compound of the formula:

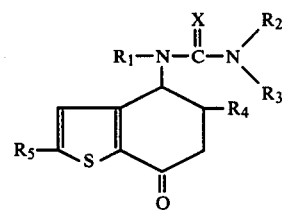

wherein X is oxygen or sulfur; $R_1$ is hydrogen or alkyl $C_1$-$C_4$; $R_3$ is selected from the group consisting of hydrogen, alkyl $C_1$-$C_4$; cycloalkyl $C_3$-$C_6$, allyl, 2-propynyl, benzyl and $\beta$-phenethyl; $R_4$ is hydrogen or alkyl $C_1$-$C_4$; $R_5$ is hydrogen, chloro, bromo or iodo; and $R_2$ is selected from the group consisting of the substituents listed in the following table:

| |
|---|
| hydrogen |
| alkyl $C_1$-$C_8$ |
| cycloalkyl $C_3$-$C_4$ |
| allyl |

-continued

| |
|---|
| 2-propynyl |
| hydroxy |
| alkoxy $C_1$-$C_6$ |
| methoxymethyl |
| phenoxy |
| 4-methoxyphenyl |

66. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

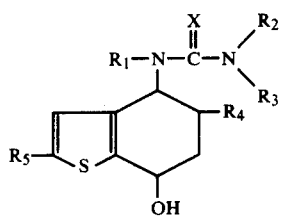

wherein X is oxygen or sulfur; $R_1$ is hydrogen or alkyl $C_1$-$C_4$; $R_3$ is selected from the group consisting of hydrogen, alkyl $C_1$-$C_4$, cycloalkyl $C_3$-$C_6$, allyl, 2-propynyl, benzyl and $\beta$-phenethyl; $R_4$ is hydrogen or alkyl $C_1$-$C_4$; $R_5$ is hydrogen, chloro, bromo or iodo; and $R_2$ is selected from the group consisting of the substituents listed in the following table:

| |
|---|
| hydrogen |
| alkyl $C_1$-$C_8$ |
| cycloalkyl $C_3$-$C_4$ |
| allyl |
| 2-propynyl |
| hydroxy |
| alkoxy $C_1$-$C_6$ |
| methoxymethyl |
| phenoxy |
| 4-methoxyphenyl |

67. The compound according to claim 1 selected from the group consisting of the dextrorotatory enantiomorph, the levorotatory enantiomorph, and the racemic mixture thereof of a compound of the formula:

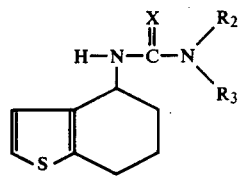

wherein X is oxygen or sulfur; $R_2$ is selected from the group consisting of hydrogen, alkyl $C_1$-$C_8$, allyl, alkoxy $C_1$-$C_4$, 2-propynyl, hydroxy and methoxymethyl; and $R_3$ is hydrogen or alkyl $C_1$-$C_4$.

68. The compound according to claim 1 selected from the group consisting of the dextrorotatory enantiomorph, the levorotatory enantiomorph, and the racemic mixture thereof of a compound of the formula:

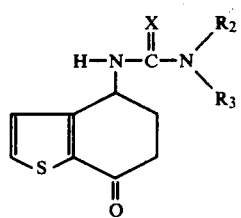

wherein X is oxygen or sulfur; $R_2$ is selected from the group consisting of hydrogen, alkyl $C_1$-$C_8$, allyl, alkoxy $C_1$-$C_4$, 2-propynyl, hydroxy and methoxymethyl; and $R_3$ is hydrogen or alkyl $C_1$-$C_4$.

69. The compound according to claim 1 selected from the group consisting of the cis-dextrorotatory enantiomorph, the cis-levorotatory enantiomorph, the racemic mixture of the cis-enantiomorphs, the trans-dextrorotatory enantiomorph, the trans-levorotatory enantiomorph, and the racemic mixture of the trans-enantiomorphs of a compound of the formula:

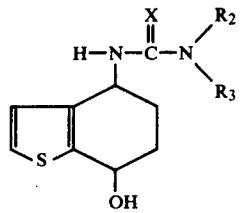

wherein X is oxygen or sulfur; $R_2$ is selected from the group consisting of hydrogen, alkyl $C_1$-$C_8$, allyl, alkoxy $C_1$-$C_4$, 2-propynyl, hydroxy and methoxymethyl; and $R_3$ is hydrogen or alkyl $C_1$-$C_4$.

* * * * *